(12) United States Patent
Boll et al.

(10) Patent No.: US 12,708,787 B2
(45) Date of Patent: Aug. 18, 2026

(54) SYSTEM AND METHOD FOR SKIN REJUVENATION USING IMPEDANCE MONITORING

(71) Applicant: Cynosure, LLC, Westford, MA (US)

(72) Inventors: James Boll, Montclair, NJ (US); Mirko Georgiev Mirkov, Chelmsford, MA (US); Daniel Masse, Windham, NH (US); Samuel Bruce, Malden, MA (US); Christian Albertelli, Salem, NH (US); James Coughlin, Ipswich, MA (US); David Sonnenshein, Dorchester, MA (US); Jeffrey Simon, Everett, MA (US)

(73) Assignee: CYNOSURE, LLC, Westford, MA (US)

( * ) Notice: Subject to any disclaimer, the term of this patent is extended or adjusted under 35 U.S.C. 154(b) by 151 days.

(21) Appl. No.: 17/319,937

(22) Filed: May 13, 2021

(65) Prior Publication Data

US 2021/0370082 A1 Dec. 2, 2021

Related U.S. Application Data

(60) Provisional application No. 63/024,483, filed on May 13, 2020.

(51) Int. Cl.
*A61N 1/40* (2006.01)

(52) U.S. Cl.
CPC .................................... *A61N 1/40* (2013.01)

(58) Field of Classification Search
CPC ........... A61N 1/40; A61N 1/327; A61N 1/328
See application file for complete search history.

(56) References Cited

U.S. PATENT DOCUMENTS

| | | |
|---|---|---|
| 853,033 A | 5/1907 | Roberts |
| 1,590,283 A | 6/1926 | Catlin |

(Continued)

FOREIGN PATENT DOCUMENTS

| | | |
|---|---|---|
| AU | 2005234703 A1 | 6/2012 |
| CN | 110693605 | 10/2020 |

(Continued)

OTHER PUBLICATIONS

Moretti, Michael, "Holmium Boosts Orthopedic Laser Development," Medical Laser Buyers Guide, p. 93 (1992).

(Continued)

*Primary Examiner* — Tammie K Marlen
(74) *Attorney, Agent, or Firm* — K&L GATES LLP

(57) ABSTRACT

In part, some embodiments described herein relate to methods of cosmetic treatment. An exemplary method may include disposing a treatment applicator comprising an electrode array comprising a plurality of needles on a portion of tissue such that a region of the electrode array contacts the portion of tissue. The method may also include applying a pulse of radio frequency (RF) energy to the portion of tissue through the electrode array; measuring impedance of electrode array over time; detecting a drop in the measured impedance while electrode array is in contact with the portion of tissue; and upon detection of the reduction in impedance by a threshold value, and terminating application of the pulse of RF energy after a treatment time period.

26 Claims, 18 Drawing Sheets
(7 of 18 Drawing Sheet(s) Filed in Color)

(56) References Cited

U.S. PATENT DOCUMENTS

| | | | |
|---|---|---|---|
| 1,676,183 | A | 7/1928 | Garfunkle |
| 1,706,161 | A | 3/1929 | Hollnagen |
| 2,068,721 | A | 1/1937 | Wappler et al. |
| 2,472,385 | A | 6/1949 | Rollman |
| 2,669,771 | A | 2/1954 | Burge et al. |
| 3,243,650 | A | 3/1966 | Hawkins et al. |
| 3,261,978 | A | 7/1966 | Brenman |
| 3,284,665 | A | 11/1966 | Goncz |
| 3,327,712 | A | 6/1967 | Kaufman |
| 3,465,203 | A | 9/1969 | Michaels et al. |
| 3,486,070 | A | 12/1969 | Engel |
| 3,524,144 | A | 8/1970 | Buser et al. |
| 3,527,932 | A | 9/1970 | Thomas |
| 3,538,919 | A | 11/1970 | Meyer |
| 3,597,652 | A | 8/1971 | Gates, Jr. |
| 3,622,743 | A | 11/1971 | Muncheryan |
| 3,651,425 | A | 3/1972 | McKnight |
| 3,653,778 | A | 4/1972 | Freiling |
| 3,667,454 | A | 6/1972 | Prince |
| 3,693,623 | A | 9/1972 | Harte et al. |
| 3,699,967 | A | 10/1972 | Anderson |
| 3,725,733 | A | 4/1973 | Mack et al. |
| 3,766,393 | A | 10/1973 | Herzog et al. |
| 3,766,488 | A | 10/1973 | Kohn |
| 3,769,963 | A | 11/1973 | Goldman et al. |
| 3,793,723 | A | 2/1974 | Kuris et al. |
| 3,794,028 | A | 2/1974 | Mueller et al. |
| 3,815,046 | A | 6/1974 | Johnson et al. |
| 3,818,373 | A | 6/1974 | Chun et al. |
| 3,818,914 | A | 6/1974 | Bender |
| 3,821,510 | A | 6/1974 | Muncheryan |
| 3,834,391 | A | 9/1974 | Block |
| 3,843,865 | A | 10/1974 | Nath |
| 3,846,811 | A | 11/1974 | Nakamura et al. |
| 3,857,015 | A | 12/1974 | Clark et al. |
| 3,858,577 | A | 1/1975 | Bass et al. |
| 3,861,921 | A | 1/1975 | Hoffmann et al. |
| 3,885,569 | A | 5/1975 | Judson |
| 3,890,537 | A | 6/1975 | Park et al. |
| 3,900,034 | A | 8/1975 | Katz et al. |
| 3,909,649 | A | 9/1975 | Arsena |
| 3,914,709 | A | 10/1975 | Pike et al. |
| 3,939,560 | A | 2/1976 | Lyall |
| 3,977,083 | A | 8/1976 | Leslie et al. |
| 3,980,861 | A | 9/1976 | Fukunaga |
| 4,019,156 | A | 4/1977 | Fountain et al. |
| 4,037,136 | A | 7/1977 | Hoene |
| 4,038,984 | A | 8/1977 | Sittner |
| 4,047,106 | A | 9/1977 | Robinson |
| 4,065,370 | A | 12/1977 | Noble et al. |
| 4,122,853 | A | 10/1978 | Smith |
| 4,133,503 | A | 1/1979 | Bliss |
| 4,139,342 | A | 2/1979 | Sheldrake et al. |
| 4,154,240 | A | 5/1979 | Ikuno et al. |
| 4,176,324 | A | 11/1979 | Aldag et al. |
| 4,188,927 | A | 2/1980 | Harris |
| 4,213,462 | A | 7/1980 | Sato |
| 4,228,800 | A | 10/1980 | Degler, Jr. et al. |
| 4,233,493 | A | 11/1980 | Nath et al. |
| 4,254,333 | A | 3/1981 | Bergstrom |
| 4,259,123 | A | 3/1981 | Tymkewicz |
| 4,269,067 | A | 5/1981 | Tynan et al. |
| 4,273,109 | A | 6/1981 | Enderby |
| 4,275,335 | A | 6/1981 | Ishida et al. |
| 4,291,281 | A | 9/1981 | Pinard et al. |
| 4,292,601 | A | 9/1981 | Aldag et al. |
| 4,293,827 | A | 10/1981 | McAllister et al. |
| 4,298,005 | A | 11/1981 | Mutzhas |
| 4,299,912 | A | 11/1981 | Shiba et al. |
| 4,302,730 | A | 11/1981 | Jernigan |
| 4,313,431 | A | 2/1982 | Frank |
| 4,316,467 | A | 2/1982 | Muckerheide |
| 4,333,197 | A | 6/1982 | Kuris |
| 4,335,726 | A | 6/1982 | Kolstedt |
| 4,336,809 | A | 6/1982 | Clark |
| 4,364,015 | A | 12/1982 | Drake et al. |
| 4,375,684 | A | 3/1983 | Everett |
| 4,388,924 | A | 6/1983 | Weissman et al. |
| 4,409,479 | A | 10/1983 | Sprague et al. |
| 4,428,368 | A | 1/1984 | Torii |
| 4,435,808 | A | 3/1984 | Javan |
| 4,445,217 | A | 4/1984 | Acharekar et al. |
| 4,452,081 | A | 6/1984 | Seppi |
| 4,456,872 | A | 6/1984 | Froeschle |
| 4,461,294 | A | 7/1984 | Baron |
| 4,488,104 | A | 12/1984 | Suzuki |
| 4,489,415 | A | 12/1984 | Jones et al. |
| 4,492,601 | A | 1/1985 | Nakasone et al. |
| 4,503,854 | A | 3/1985 | Jako |
| 4,504,727 | A | 3/1985 | Melcher et al. |
| 4,512,197 | A | 4/1985 | von Gutfeld et al. |
| 4,524,289 | A | 6/1985 | Hammond et al. |
| 4,539,987 | A | 9/1985 | Nath et al. |
| 4,553,546 | A | 11/1985 | Javelle |
| 4,555,786 | A | 11/1985 | Byer |
| 4,556,979 | A | 12/1985 | Scott et al. |
| 4,559,943 | A | 12/1985 | Bowers |
| 4,561,440 | A | 12/1985 | Kubo et al. |
| 4,566,271 | A | 1/1986 | French et al. |
| 4,566,438 | A | 1/1986 | Liese et al. |
| 4,569,345 | A | 2/1986 | Manes |
| 4,576,177 | A | 3/1986 | Webster, Jr. |
| 4,587,968 | A | 5/1986 | Price |
| 4,591,762 | A | 5/1986 | Nakamura |
| 4,592,353 | A | 6/1986 | Daikuzono |
| 4,601,037 | A | 7/1986 | McDonald |
| 4,601,753 | A | 7/1986 | Soileau et al. |
| 4,608,978 | A | 9/1986 | Rohr |
| 4,608,979 | A | 9/1986 | Breidenthal et al. |
| 4,617,926 | A | 10/1986 | Sutton |
| 4,623,929 | A | 11/1986 | Johnson et al. |
| 4,629,884 | A | 12/1986 | Bergstrom |
| 4,638,800 | A | 1/1987 | Michel |
| 4,653,495 | A | 3/1987 | Nanaumi |
| 4,656,641 | A | 4/1987 | Scifres et al. |
| 4,662,368 | A | 5/1987 | Hussein et al. |
| 4,676,231 | A | 6/1987 | Hisazumi et al. |
| 4,677,347 | A | 6/1987 | Nakamura |
| 4,686,986 | A | 8/1987 | Fenyo |
| 4,693,244 | A | 9/1987 | Daikuzono |
| 4,693,556 | A | 9/1987 | McCaughan, Jr. |
| 4,695,697 | A | 9/1987 | Kosa |
| 4,710,677 | A | 12/1987 | Halberstadt et al. |
| 4,718,416 | A | 1/1988 | Nanaumi |
| 4,724,835 | A | 2/1988 | Liss et al. |
| 4,733,660 | A | 3/1988 | Itzkan |
| 4,735,201 | A | 4/1988 | O'Reilly |
| 4,736,743 | A | 4/1988 | Daikuzono |
| 4,736,745 | A | 4/1988 | Gluckman |
| 4,740,047 | A | 4/1988 | Abe et al. |
| 4,741,338 | A | 5/1988 | Miyamae |
| 4,745,909 | A | 5/1988 | Pelton et al. |
| 4,747,660 | A | 5/1988 | Nishioka et al. |
| 4,749,913 | A | 6/1988 | Stuermer et al. |
| 4,759,349 | A | 7/1988 | Betz et al. |
| 4,773,413 | A | 9/1988 | Hussein et al. |
| 4,775,361 | A | 10/1988 | Jacques et al. |
| 4,779,173 | A | 10/1988 | Carr et al. |
| 4,784,135 | A | 11/1988 | Blum et al. |
| 4,799,479 | A | 1/1989 | Spears |
| 4,813,412 | A | 3/1989 | Yamazaki et al. |
| 4,813,762 | A | 3/1989 | Leger et al. |
| 4,819,669 | A | 4/1989 | Politzer |
| 4,826,431 | A | 5/1989 | Fujimura et al. |
| 4,829,262 | A | 5/1989 | Furumoto |
| 4,832,024 | A | 5/1989 | Boussignac et al. |
| 4,840,174 | A | 6/1989 | Gluckman |
| 4,840,563 | A | 6/1989 | Altendorf |
| 4,845,608 | A | 7/1989 | Gdula |
| 4,848,339 | A | 7/1989 | Rink et al. |
| 4,852,107 | A | 7/1989 | Hamal et al. |
| 4,852,549 | A | 8/1989 | Mori |
| 4,860,172 | A | 8/1989 | Schlager et al. |
| 4,860,303 | A | 8/1989 | Russell |

(56) References Cited

U.S. PATENT DOCUMENTS 4,860,743 A 8/1989 Abela
4,860,744 A 8/1989 Johnson et al.
4,862,886 A 9/1989 Clarke et al.
4,862,888 A 9/1989 Yessik
4,862,903 A 9/1989 Campbell
4,871,479 A 10/1989 Bachelard et al.
4,878,224 A 10/1989 Kuder
4,884,560 A 12/1989 Kuracino
4,887,600 A 12/1989 Watson et al.
4,889,525 A 12/1989 Yuhas et al.
4,890,898 A 1/1990 Bentley et al.
4,891,817 A 1/1990 Duarte
4,896,329 A 1/1990 Knaak
4,898,438 A 2/1990 Mori
4,898,439 A 2/1990 Mori
4,901,323 A 2/1990 Hawkins et al.
4,905,690 A 3/1990 Oshiro et al.
4,910,438 A 3/1990 Farnsworth
4,913,142 A 4/1990 Kittrell et al.
4,914,298 A 4/1990 Quad et al.
4,917,084 A 4/1990 Sinofsky
4,926,227 A 5/1990 Jensen
4,928,038 A 5/1990 Nerone
4,930,504 A 6/1990 Diamantopoulos
4,931,053 A 6/1990 L'Esperance
4,932,954 A 6/1990 Wondrazek et al.
4,945,239 A 7/1990 Wist et al.
4,950,266 A 8/1990 Sinofsky
4,955,882 A 9/1990 Hakky
4,968,314 A 11/1990 Michaels
4,972,427 A 11/1990 Streifer et al.
4,973,848 A 11/1990 Kolobanov et al.
4,974,587 A 12/1990 Turner et al.
4,976,308 A 12/1990 Faghri
4,976,709 A 12/1990 Sand
4,977,571 A 12/1990 Furumoto et al.
4,978,186 A 12/1990 Mori
4,979,180 A 12/1990 Muncheryan
4,992,256 A 2/1991 Skaggs et al.
4,994,060 A 2/1991 Rink et al.
5,000,752 A 3/1991 Hoskin et al.
5,006,293 A 4/1991 Hartman et al.
5,009,658 A 4/1991 Damgaard-Iverson
5,011,483 A 4/1991 Sleister
5,027,359 A 6/1991 Leger et al.
5,029,588 A 7/1991 Yock et al.
5,030,090 A 7/1991 Maeda et al.
5,032,178 A 7/1991 Cornell
5,037,421 A 8/1991 Boutacoff et al.
5,041,109 A 8/1991 Abela
5,046,494 A 9/1991 Searfoss et al.
5,050,597 A 9/1991 Daikuzono
5,056,515 A 10/1991 Abel
5,057,099 A 10/1991 Rink
5,057,104 A 10/1991 Chess
5,059,192 A 10/1991 Zaias
5,060,243 A 10/1991 Eckert
5,061,265 A 10/1991 Abela et al.
5,061,266 A 10/1991 Hakky
5,065,515 A 11/1991 Iderosa
5,066,292 A 11/1991 Müller et al.
5,066,293 A 11/1991 Furumoto
5,071,416 A 12/1991 Heller et al.
5,071,417 A 12/1991 Sinofsky
5,080,660 A 1/1992 Buelna
5,090,019 A 2/1992 Scheps
5,092,865 A 3/1992 Rink
5,099,231 A 3/1992 Sato
5,102,410 A 4/1992 Dressel
5,108,388 A 4/1992 Trokel
5,109,387 A 4/1992 Garden et al.
5,112,328 A 5/1992 Taboada et al.
5,127,395 A 7/1992 Bontemps
5,129,896 A 7/1992 Hasson
5,129,897 A 7/1992 Daikuzono
5,132,980 A 7/1992 Connors et al.
5,133,102 A 7/1992 Sakuma
5,137,530 A 8/1992 Sand
5,140,608 A 8/1992 Karpol et al.
5,140,984 A 8/1992 Dew et al.
5,147,353 A 9/1992 Everett
5,147,356 A 9/1992 Bhatta
5,151,097 A 9/1992 Daikuzono
5,159,601 A 10/1992 Huber
5,160,194 A 11/1992 Feldman
5,163,935 A 11/1992 Black et al.
5,171,564 A 12/1992 Nathoo et al.
5,178,617 A 1/1993 Kuizenga et al.
5,180,378 A 1/1993 Kung et al.
5,182,557 A 1/1993 Lang
5,182,857 A 2/1993 Simon
5,190,541 A 3/1993 Abele et al.
5,191,883 A 3/1993 Lennox et al.
5,192,278 A 3/1993 Hayes et al.
5,193,526 A 3/1993 Daikuzono
5,196,004 A 3/1993 Sinofsky
5,197,470 A 3/1993 Helfer et al.
5,201,731 A 4/1993 Hakky
5,207,671 A 5/1993 Franken et al.
5,207,672 A 5/1993 Roth et al.
5,207,673 A 5/1993 Ebling et al.
5,209,748 A 5/1993 Daikuzono
5,213,092 A 5/1993 Uram
5,217,455 A 6/1993 Tan
5,219,347 A 6/1993 Negus et al.
5,222,907 A 6/1993 Katabuchi et al.
5,222,953 A 6/1993 Dowlatshaki
5,225,926 A 7/1993 Cuomo et al.
5,226,907 A 7/1993 Tankovich
5,242,437 A 9/1993 Everett et al.
5,242,438 A 9/1993 Saadatmanesh
5,246,436 A 9/1993 Rowe
5,249,192 A 9/1993 Kuizenga et al.
5,254,114 A 10/1993 Reed, Jr. et al.
5,255,277 A 10/1993 Carvalho
5,257,970 A 11/1993 Dougherty
5,257,991 A 11/1993 Fletcher et al.
5,261,904 A 11/1993 Baker et al.
5,267,399 A 12/1993 Johnston
5,267,995 A 12/1993 Doiron et al.
5,267,998 A 12/1993 Hagen
5,269,777 A 12/1993 Doiron et al.
5,269,780 A 12/1993 Roos
5,281,211 A 1/1994 Parel et al.
5,281,216 A 1/1994 Klicek
5,282,797 A 2/1994 Chess
5,284,154 A 2/1994 Raymond et al.
5,287,372 A 2/1994 Ortiz
5,287,380 A 2/1994 Hsia
5,290,273 A 3/1994 Tan
5,290,274 A 3/1994 Levy et al.
5,292,320 A 3/1994 Brown et al.
5,293,880 A 3/1994 Levitt
5,300,063 A 4/1994 Tano et al.
5,300,065 A 4/1994 Anderson
5,300,097 A 4/1994 Lerner et al.
5,303,324 A 4/1994 Lundahl
5,303,585 A 4/1994 Lichte
5,304,167 A 4/1994 Freiberg
5,304,170 A 4/1994 Green
5,304,173 A 4/1994 Kittrell et al.
5,306,143 A 4/1994 Levy
5,306,274 A 4/1994 Long
5,307,369 A 4/1994 Kimberlin
5,308,311 A 5/1994 Eggers et al.
5,312,395 A 5/1994 Tan et al.
5,312,396 A 5/1994 Feld et al.
5,320,618 A 6/1994 Gustafsson
5,320,620 A 6/1994 Long et al.
5,330,470 A 7/1994 Hagen
5,331,649 A 7/1994 Dacquay et al.
5,334,191 A 8/1994 Poppas et al.
5,334,193 A 8/1994 Nardella
5,336,217 A 8/1994 Buys et al.

(56) References Cited

U.S. PATENT DOCUMENTS 5,336,221 A 8/1994 Anderson
5,342,358 A 8/1994 Daikuzono et al.
5,344,418 A 9/1994 Ghaffari
5,344,434 A 9/1994 Talmore
5,346,488 A 9/1994 Prince et al.
5,348,551 A 9/1994 Spears et al.
5,349,590 A 9/1994 Amirkhanian et al.
5,350,376 A 9/1994 Brown
5,353,020 A 10/1994 Schurmann
5,353,790 A 10/1994 Jacques et al.
5,354,294 A 10/1994 Chou
5,356,081 A 10/1994 Sellar
5,358,503 A 10/1994 Bertwell et al.
5,360,426 A 11/1994 Muller et al.
5,366,456 A 11/1994 Rink et al.
5,368,031 A 11/1994 Cline et al.
5,368,038 A 11/1994 Fraden
5,369,496 A 11/1994 Alfano et al.
5,369,831 A 12/1994 Bock
5,370,642 A 12/1994 Keller
5,370,649 A 12/1994 Gardetto et al.
5,380,317 A 1/1995 Everett et al.
5,383,876 A 1/1995 Nardella
5,386,427 A 1/1995 Zayhowski
5,387,211 A 2/1995 Saadatmanesh
5,395,356 A 3/1995 King et al.
5,403,306 A 4/1995 Edwards et al.
5,403,308 A 4/1995 Wood et al.
5,405,368 A 4/1995 Eckhouse
5,409,446 A 4/1995 Rattner
5,409,479 A 4/1995 Dew et al.
5,409,481 A 4/1995 Poppas et al.
5,415,654 A 5/1995 Daikuzono
5,421,337 A 6/1995 Richards-Kortum
5,421,339 A 6/1995 Ramanujam et al.
5,422,112 A 6/1995 Williams
5,423,800 A 6/1995 Ren et al.
5,423,803 A 6/1995 Tankovich et al.
5,423,805 A 6/1995 Brucker et al.
5,425,728 A 6/1995 Tankovich
5,425,735 A 6/1995 Rosen et al.
5,425,754 A 6/1995 Braun et al.
5,437,660 A 8/1995 Johnson et al.
5,439,954 A 8/1995 Bush
5,441,499 A 8/1995 Fritzsch
5,445,608 A 8/1995 Chen et al.
5,445,611 A 8/1995 Eppstein et al.
5,454,807 A 10/1995 Lennox et al.
5,456,682 A 10/1995 Edwards et al.
5,458,140 A 10/1995 Eppstein et al.
5,464,436 A 11/1995 Smith
5,464,724 A 11/1995 Akiyama et al.
5,470,331 A 11/1995 Daikuzono
5,472,748 A 12/1995 Wolfe et al.
5,474,549 A 12/1995 Ortiz et al.
5,484,436 A 1/1996 Eggers et al.
5,486,170 A 1/1996 Winston et al.
5,486,172 A 1/1996 Chess
5,588,952 A 12/1996 Dandolu
5,733,277 A 3/1998 Pallarito
5,876,397 A 3/1999 Edelman et al.
6,096,030 A 8/2000 Ortiz
6,113,589 A 9/2000 Levy et al.
6,143,018 A 11/2000 Beuthan et al.
6,174,424 B1 1/2001 Wach et al.
6,277,116 B1 8/2001 Utely et al.
6,343,174 B1 1/2002 Neuberger
6,413,255 B1 7/2002 Stern
6,432,101 B1 8/2002 Weber et al.
6,440,121 B1 8/2002 Weber et al.
6,662,054 B2 12/2003 Kreindel et al.
6,702,808 B1 3/2004 Kreindel
6,723,091 B2 4/2004 Goble et al.
6,904,323 B2 6/2005 Samulski
7,022,121 B2 4/2006 Stern et al.
7,062,317 B2 6/2006 Avrahami et al.
7,141,049 B2 11/2006 Stern et al.
7,229,436 B2 6/2007 Stern et al.
7,238,183 B2 7/2007 Kreindel
7,300,436 B2 11/2007 Penny et al.
7,335,199 B2 2/2008 Goble et al.
7,452,358 B2 11/2008 Stern et al.
7,494,488 B2 2/2009 Weber
7,643,883 B2 1/2010 Kreindel
7,713,266 B2 5/2010 Elkins et al.
7,857,775 B2 12/2010 Rosenberg et al.
7,947,037 B1 5/2011 Garito et al.
7,955,262 B2 6/2011 Rosenberg
8,007,493 B2 8/2011 McGill et al.
8,133,216 B2 3/2012 Knopp et al.
8,142,426 B2 3/2012 Knopp et al.
8,150,532 B2 4/2012 Karni et al.
8,206,381 B2 6/2012 Lischinsky et al.
8,216,215 B2 7/2012 Flyash et al.
8,273,037 B2 9/2012 Kreindel et al.
8,273,080 B2 9/2012 Mehta
8,321,031 B1 11/2012 Ellman et al.
8,357,146 B2 1/2013 Hennings et al.
8,357,150 B2 1/2013 Adanny et al.
8,435,194 B2 5/2013 Dverin et al.
8,496,654 B2 7/2013 Adanny et al.
8,515,542 B2 8/2013 Jaax et al.
8,603,088 B2 12/2013 Stern et al.
8,606,366 B2 12/2013 Flyash et al.
8,641,703 B2 2/2014 Flyash et al.
8,652,130 B2 2/2014 Kreindel
8,702,769 B2 4/2014 Eckhouse et al.
8,728,071 B2 5/2014 Lischinsky et al.
9,011,419 B2 4/2015 Flyash et al.
9,028,480 B2 5/2015 Adanny et al.
9,072,882 B2 7/2015 Adanny et al.
9,084,587 B2 7/2015 Eckhouse et al.
9,108,036 B2 8/2015 Adanny et al.
9,161,802 B2 10/2015 Przybyszewski
9,168,096 B2 10/2015 Kreindel
9,227,081 B2 1/2016 Adanny et al.
9,247,985 B2 2/2016 Govari et al.
9,277,958 B2 3/2016 Schomacker et al.
9,280,329 B2 3/2016 Brown et al.
9,314,293 B2 4/2016 Rosenberg
9,314,650 B2 4/2016 Rosenberg et al.
9,326,910 B2 5/2016 Eckhouse et al.
9,345,531 B2 5/2016 Furnish et al.
9,381,057 B2 7/2016 Schomacker et al.
9,415,236 B2 8/2016 Adanny et al.
9,433,781 B2 9/2016 Eckhous et al.
9,446,258 B1 9/2016 Schwarz et al.
9,468,774 B2 10/2016 Zársky et al.
9,504,826 B2 11/2016 Flyash et al.
9,532,832 B2 1/2017 Ron Edoute et al.
9,585,687 B2 3/2017 Tenenbaum et al.
9,597,528 B2 3/2017 Schomacker et al.
9,827,437 B2 11/2017 Lischinsky et al.
9,844,682 B2 12/2017 Lischinsky et al.
9,889,297 B2 2/2018 Schomacker
9,895,188 B2 2/2018 Schomacker et al.
9,981,143 B2 5/2018 Ron Edoute et al.
10,124,187 B2 11/2018 Schwarz et al.
10,195,453 B2 2/2019 Schwarz et al.
10,322,296 B2 6/2019 Adanny et al.
10,420,602 B2 9/2019 Horton et al.
10,561,570 B2 2/2020 Eckhouse et al.
10,799,712 B2 10/2020 Anderson, Jr. et al.
10,849,784 B2 12/2020 Jurna et al.
10,881,882 B1 1/2021 Schwarz et al.
10,933,250 B2 3/2021 Eisenmann et al.
10,946,192 B2 3/2021 Palero et al.
10,953,235 B2 3/2021 Anderson et al.
11,045,249 B2 6/2021 Britva et al.
11,179,565 B2 11/2021 Palero et al.
2001/0012429 A1 8/2001 Wach et al.
2001/0056278 A1 12/2001 Nield et al.
2002/0062142 A1* 5/2002 Knowlton .............. A61B 90/02
607/104

(56) References Cited

U.S. PATENT DOCUMENTS

2002/0099293 A1 7/2002 Fontenot et al.
2002/0183728 A1 12/2002 Rosenberg et al.
2003/0092176 A1 5/2003 Janson et al.
2003/0139740 A1 7/2003 Kreindel
2003/0195592 A1 10/2003 Black
2006/0036300 A1 2/2006 Kreindel
2006/0045489 A1 3/2006 Evans et al.
2006/0047281 A1 3/2006 Kreindel
2006/0206110 A1 9/2006 Knowlton et al.
2007/0129714 A1 6/2007 Elkins et al.
2007/0142885 A1 6/2007 Hantash et al.
2007/0191827 A1 8/2007 Lischinsky et al.
2007/0219540 A1 9/2007 Masotti et al.
2007/0263975 A1 11/2007 Boutoussov et al.
2008/0091185 A1 4/2008 McGill et al.
2008/0188835 A1 8/2008 Hennings et al.
2008/0269375 A1 10/2008 Park et al.
2009/0130622 A1 5/2009 Bollinger et al.
2009/0171424 A1 7/2009 Britva et al.
2009/0221938 A1 9/2009 Rosenberg et al.
2009/0254076 A1 10/2009 Altshuler et al.
2009/0326571 A1 12/2009 Mulholland
2010/0063493 A1 3/2010 Anastasie
2010/0106064 A1 4/2010 Kreindel et al.
2010/0204619 A1 8/2010 Rosenberg
2010/0217254 A1 8/2010 Mehta
2010/0286672 A1 11/2010 Walker et al.
2011/0015625 A1 1/2011 Adanny et al.
2011/0121735 A1 5/2011 Penny
2011/0144729 A1 6/2011 Weber
2011/0160713 A1 6/2011 Neuberger
2011/0190726 A1 8/2011 Hantash et al.
2011/0208183 A1* 8/2011 Stockert ................ A61B 18/16
606/35
2011/0301584 A1 12/2011 Beck et al.
2012/0022627 A1 1/2012 Adanny et al.
2012/0136282 A1 5/2012 Rosenberg et al.
2012/0150168 A1 6/2012 Adanny et al.
2012/0150174 A1 6/2012 Adanny et al.
2012/0158100 A1 6/2012 Schomacker
2012/0310311 A1 12/2012 Elkah
2013/0289679 A1 10/2013 Eckhouse et al.
2014/0005658 A1 1/2014 Rosenberg
2014/0025033 A1 1/2014 Mirkov et al.
2014/0025062 A1 1/2014 Rosenberg et al.
2014/0309628 A1 10/2014 Vaynberg et al.
2015/0038965 A1 2/2015 Iger
2015/0265492 A1 9/2015 Eckhouse et al.
2015/0328474 A1 11/2015 Flyash et al.
2016/0114181 A1 4/2016 Vaynberg et al.
2016/0158574 A1 6/2016 Eckhouse et al.
2016/0228698 A1 8/2016 Horton et al.
2016/0263388 A1 9/2016 Alinsod et al.
2017/0136237 A1 5/2017 Eckhouse et al.
2017/0189668 A1 7/2017 Jurna et al.
2017/0266457 A1 9/2017 Eckhouse et al.
2017/0304641 A1 10/2017 Eisenmann et al.
2017/0319262 A1 11/2017 Palero et al.
2018/0000533 A1* 1/2018 Boll .................. A61B 18/1485
2018/0064575 A1 3/2018 Vaynberg et al.
2018/0103991 A1 4/2018 Linhart et al.
2018/0133469 A1 5/2018 Palero et al.
2018/0207421 A1 7/2018 Jurna et al.
2018/0271597 A1 9/2018 Eisenmann et al.
2019/0133673 A1 5/2019 Boll et al.
2019/0134414 A1 5/2019 Prouza et al.
2020/0016422 A1 1/2020 Ron Edoute et al.
2020/0016423 A1 1/2020 Ron Edoute et al.
2020/0261736 A1 8/2020 Berube et al.
2020/0324133 A1 10/2020 Schwarz et al.
2020/0352633 A1 11/2020 Treen et al.
2021/0146119 A1 5/2021 Prouza et al.
2021/0196342 A1 7/2021 Ko et al.
2021/0204996 A1* 7/2021 Ko ........................ A61B 5/053
2021/0268299 A1 9/2021 Casalino et al.
2021/0275825 A1 9/2021 Kreindel
2022/0409259 A1 12/2022 Ko

FOREIGN PATENT DOCUMENTS

CN 112691293 4/2021
CN 112843476 5/2021
EP 2614807 7/2013
EP 2291223 1/2016
EP 3481495 4/2020
GB 0004179 4/2000
JP 2000237022 9/2000
JP 2003529401 10/2003
JP 2007536963 12/2007
KR 101743706 5/2013
KR 101314574 10/2013
KR 20170002785 8/2017
KR 101860803 1/2018
KR 20180010825 1/2018
KR 20190011797 2/2019
KR 20190114772 2/2019
KR 102048384 1/2020
KR 102114838 6/2020
KR 102140561 8/2020
KR 20210110853 9/2021
WO 0113989 3/2001
WO 2001069731 A3 9/2001
WO 2007013072 2/2007
WO 2008068749 A1 6/2008
WO 2008114255 9/2008
WO 20080153999 12/2008
WO 2010097790 A1 9/2010
WO 2012063236 5/2012
WO 2012144712 10/2012
WO 2014072866 5/2014
WO 2018008023 1/2018
WO 2018016819 1/2018
WO 2018/182188 10/2018
WO 2019225897 11/2019
WO 2020142470 7/2020
WO 20211054664 3/2021
WO 2021144754 7/2021
WO 2021150385 7/2021

OTHER PUBLICATIONS

Moretti, Michael, "Lasers Improve Prostatectomy Treatment," Medical Laser Buyers Guide, p. 94-96 (1992).
Mostovnikov, V.A. et al., "Recovery of Lasing Properties of Dye Solutions after Their Photolysis," Sov. J. Quantum Electron, 6(9), Sep. 1976, pp. 1126-1128.
Nanni, C.A. et al., "Complications of Carbon Dioxide Laser Resurfacing," Washington Inst. of Dermatol. Surg. 24:315-320 (1998).
Nemeth, et al., "Copper vapor laser treatment of pigmented lesions," Lasers Surg. Med. Supp. 2:51 (1990).
Ogiso et al., "Phase Transitions of Rat Stratum Corneum Lipids By an Electron Paramagnetic Resonance Study and Relationship of Phase States to Drug Penetration," Biochimica et Biophysica Acta 1301:97-104 (1996).
Ohbayashi, "Stimulatory Effect of Laser Irradiation on Calcified Nodule Formation in Human Dental Pulp Fibroblasts," Abstract J-Endod. Jan. 1999; 25(1): 30-3.
Ohshiro et al., "The Ruby and Argon Lasers in the Treatment of the Naevi," Annals Academy of Medicine, Apr. 1983, vol. 12, No. 2, pp. 388-395.
Oleinik, et al., "Automatized Securing Definition for Laser Therapy Indications in Case of Non-complicated Caries," SPIE, vol. 1984, pp. 238-244.
Oraevsky, Alexander A. et al., "Plasma Mediated Ablation of Biological Tissues with Nanosecond-to-Femtosecond Laser Pulses: Relative Role of Lineear and Nonlinear Absorption," IEEE Journal of Selected Topics in Quantum Electronics, vol. 2, No. 4, Dec. 1996, pp. 801-809.
Orchardson, "Effect of Pulsed Nd:YAG Laser Radiation on Action Potential Conduction in Nerve Fibres Inside Teeth in vitro," ABSTRACT J-Dent. Jul-Aug. 1998; 26(5-6): 421-6.

(56) References Cited

OTHER PUBLICATIONS

Overholt Bf et al. "Balloon photodynamic therapy of esophageal cancer: effect of increasing balloon size," PubMed; Lasers Surg Med. 1996, 18(3):248-52.
Ozawa et al., "Stimulatory Effects of Low-Power Laser Irradiation on Bone Formation in vitro," SPIE vol. 1984, pp. 281-288.
Panjehpour M et al. "Spectroscopic diagnosis of esophageal cancer: new classification model, improved measurement system," PubMed; Gastrointest Endosc. 1995, Jun. 41 (6):577-81.
Parrish, J.A., "Selective thermal effects with pulsed irradiation from lasers: From organ to organelle," Journal of Investigative Dermatology, vol. 80, No. 6 Supplement, pp. 75s-80s, 1983.
Petrischev et al. "Clinical and Experimental Low-Intense Laser Therapy in Dentistry," SPIE, vol. 1984, pp. 212-214.
Petrischev et al., "Report on Low Intensity Laser Radiation Usage in Dentistry," SPIE vol. 1984, pp. 202-211.
Polanyi, Thomas & Tobias, Irwin, Lasers-A Series of Advances, Edited by A.K. Levine, vol. 2, Marcel Dekker, Inc, N. Y., 1968, pp. 400, 402-403 & 422.
Polla, L. et al., "Melanosomes are a primary target of Q-switched ruby laser irradiation in guinea pig skin," Journal of Investigative Dermatology, vol. 89, No. 3, pp. 281-286, Sep. 1987.
Powell, "Laser Dental Decay Prevention: does it have a future?" SPIE vol. 3192, 1997.
Reed J.T et al., "Treatment of Periorbital Wrinkles," Washington Inst. of Dermatol. Surg. 23:643-648 (1997).
Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).
Remillard et al., "Diode Laser Illuminators for Night-Vision Applications," SPIE Proceedings vol. 4285:14-22 (2001).
Riggle et al., "Laser Effects on Normal and Tumor Tissue," Laser Applications in Medicine and Biology, vol. 1, M.L. Wolbarsht, editor, Plenum Press, publishers, Ch. 3, pp. 35-65 (1971).
Rohrer, "Evaluating the Safety and Efficacy of a Novel Light Based Hair Removal System, " Lasers. Surg. Med. Supp. 13:97 (2001).
Rosenfeld, H., et al., "Treatment of Cutaneous and Deep Vascular Lesions with the Nd:YAG Laser," Lasers in Surgery and Medicine, 6:20-23 (1986).
Rotteleur, et al., "Robotized scanning laser handpiece for the treatment of port wine stains and other angiodysplasias," Lasers Surg. Med., 8:283-287 (1998).
Rubach et al., "Histological and Clinical Evaluation of Facial Resurfacing Using a Carbon Dioxide Laser With the Computer Pattern Generator," Arch Otolaryngol Head Neck Surg., 123:929-934 (1997).
Russel et al. "Flash-Lamp-Excited Self-Injection-Seeded Q-Switch Ti:Al2O3 Laser Oscillator," Applied Optics, vol. 35, No. 24 (Aug. 1996).
Rylander, C.G et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).
Sandford et al., "Thermal Effects During Desensitisation of Teeth with Gallium-Aluminum-Arsenide Lasers," University of Queensland Dental School, Periodontology 15: 25-30 (1994).
Schade, W. et al., "Temperature tuned distributed feedback dye laser with high repetition rate," Applied Optics, vol. 2 9, No. 27, Sep. 20, 1990, pp. 3950-3954.
Schappert et al., "Temperature Tuning of an Organic Dye Laser," Applied Physics Letters 13(4): 124-126 (Aug. 15, 1968).
Schindl, "Does Low Intensity Laser Irradiation Really Cause Cell Damage?" Laser in Surgery and Medicine vol. 22, pp. 105, 2001.
Sheehan-Dare, et al., "Lasers in Dermatology," British Journal of Dermatology, 129:1-8 (1993).
Shimbashi, T et al., "Ruby laser treatment of pigmented skin lesions," Aesth. Plast. Surg., vol. 19, pp. 225-229, 1995.
Shimizu et al., "Prospect of Relieving Pain Due to Tooth Movement During Orthodontic Treatment Utilizing a GA-Al as Diode Laser," SPIE vol. 1984, pp. 275-280.
Shumilovitch et al., "Influence of Low Intensity Laser Radiation Upon the Microflora of Carious Cavities and Root Canal," SPIE vol. 1984, pp. 215-220.
Shuster, "Acne: The Ashes of a Burnt Out Controversy," Acta Derm. Venereol. Suppl. (Stockh), 120:43-46, 1985.
Sigurdsson et al., "Phototherapy of Acne Vulgaris with Visible Light," Dermatology, 194:256-260, 1997.
Sing, "Electroacupuncture and Laser Stimulation Treatment: Evaluation by Somatosensory Evoked Potential in Conscious Rabbits," Abstract AM-J-Chin-Med. 1997; 25(3-4): 263-71.
Sliney et al., "Safety with Lasers and Other Optical Sources: A Comprehensive Handbook," Plenum Press, pp. 477-480 (1980).
Sokolova et al., "Low-intense Laser Radiation in Complex Treatment of Inflammatory Diseases of Parodontium," SPIE vol. 1984, pp. 234-237.
Spears et al., "Fluorescence of Experimental Atheromatous Plaques with Hematoporphyrin Derivative," J. Clin. Invest, 71:395-399 (1983).
Spotswood, "Novel Use of Fractional Lasers for Scarring Improves Quality of Life for Injured Troops," http://www.usmedicine.com/articles/novel-use-of-fractional-lasers-for-scarring-improves-quality-of-life-for-injured-troops-.html, (Aug. 2012) , U.S. Medicine ISSN: 0191-6246, 4 pages.
Stratton, K. et al., "Biological Effects of Laser Radiation II: ESR Studies of Melanin Containing Tissues after Laser Irradiation," Northeast Electronics Research and Engineering Meeting-NEREM Record, IEEE Catalogue No. F-60, pp. 150-151, Nov. 1965.
Strauss et al., "Skin Lipids and Acne," Annu. Rev. Med., 26: 27-31, 1975.
Sumian, C.C. et al., "A Preliminary Clinical and Histopathological Study of Laser Skin Resurfacing Using A frequency-Doubled Nd:YAG Laser After Application of Chromofilm®," Journal of Cutaneous Laser Therapy, vol. 1, pp. 159-166, 1999.
Sumian, C.C. et al., "Laser Skin Resurfacing Using a Frequency Doubled Nd:YAG Laser After Topical Application of an Exogenous Chromophore," Lasers in Surgery and Medicine, vol. 25, pp. 43-50, 1999.
Sumian et al., "A new method to improve penetration depth of dyes into the follicular duct: Potential application for laser hair removal," J. Am. Acad. Dermotol., 41(2) Part 1:172-175, 1999.
Habbema, Louis et al., "Minimally invasive non-thermal laser technology using laser-induced optical breakdown fir skin rejuvenation", J. Biophotonics, vol. 5, No. 2, 2012, pp. 194-199.
Haedersal, et el., "Fractional Nonablative 1540 nm Laser Resurfacing for Thermal Burn Scars: A Randomized Controlled Trial", Lasers in Surgery and Medicine, 41:189-195, 2009, 7 pages.
Hicks et al., "After Low Fluence Argon Laser and Fluoride Treatment," Compendium, vol. 18, No. 6, Jun. 1997.
Hicks et al., "Enamel Caries Initiation and Progression Following Low Fluence (energy) and Argon Laser and Fluoride Treatment," The Journal of Clinical Pediatric Dentistry, vol. 20, No. 1 pp. 9-13, 1995.
Hsu et al., "Combined Effects of Laser Irradiation/Solution Flouride lon on Enamel Demineralization," Journal of Clinical Laser Medicine and Surgery, vol. 16, No. 2 pp. 93-105, 1998.
Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).
Hulsbergen Henning et al., "Port Wine Stain Coagulation Experiments with a 540-nm Continuous Wave Dye-Laser," Lasers in Surgery and Medicine, 2:205-210 (1983).
Invention description to certificate of authorship, No. 719439, "The ring resonator of optical quantum generator" (Aug. 15, 1975).
Invention description to certificate of authorship, No. 741747, "The modulator of optical radiation intensity" (Oct. 10, 1977).
Invention description to certificate of authorship, No. SU 1257475 A1, "Laser interferometric device to determine no-linearity of an index of refraction of optical medium" (Sep. 15, 1986).

(56) References Cited

OTHER PUBLICATIONS

Invention description to certificate of authorship, No. SU 1326962 A1, "The way of determination of non-linearity of an Index of refraction of optical medium" (Jul. 30, 1987).
Invention description to certificate of authorship, No. 532304, "The way of investigation of radiation time structure of optical quantum generator" (Jul. 9, 1974).
Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).
Johnsson et al., "No. photoinactivation of Propionibacterium acnes with soft laser treatment," Dermatologica, 175 (1):50, 1987.
Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.
Kandel, Laurence B., M.D., et al., "Transurethral Laser Prostatectomy in the Canine Model," Lasers in Surgery and Medicine, 12:33-42 (1992).
Kantor et al., "Treatment of acne keloidalis nuchae with carbon dioxide laser," J. Am. Acad. Dermatol., 14:263-267, 1986.
Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.
Karu, "Photobiological Fundamentals of Low-Power Laser Therapy," 8th Congress of International Society for Laser Surgery and Medicine, Mar. 30, 1987.
Kazmina et al., "Laser Prophlaxis and Treatment of Primary caries," SPIE vol. 1984, pp. 231-233.
Kelly et al., "Nonablative Laser Treatment of Facial Rhytides: United States Phase II Clinical Study," American Society for Laser Medicine and Surgery Abstracts, 10(33):38 (1998).
Kilmer et al., "Pulse Dye Laser Treatment of Rhytids," American Society for Laser Medicine and Surgery Abstracts, p. 44 (Apr. 1997).
Klein, E. et al., "Biological effects of laser radiation 1.,"Northeast Electroncis Research and Engineering Meeting, NEREM Record, IEEE catalogue No. F-60, pp. 108-109, 1965.
Kliewer, Michael L. et al., "Excited State Absorption of Pump Radiation as a Loss Mechanism in Solid-State Lasers", IEEE Journal of Quantum Electronics, vol. 25, 1989, pp. 1850-1854.
Korobov et al., "Dependence of the Quantum Yield of Intercombinational Conversion into the Triplet State of Rhodamine 6G on the pH of the Medium", Zhur. Prikl. Spektrosk. 24(1) 28-31 (Jan. 1976).
Kozlov et al., "Laser in Diagnostics and Treatment of Microcirculation Disorders Under Parodontitis," SPIE vol. 1984, pp. 253-264.
Krames et al. "Status and Future of High-Power Light-Emitting Diodes for Solid State Lighting", J. Display Technol., 3 (2):160-175 (Jun. 2007).
Kuhns, J.G. et al., "Biological effects of laser radiation II Effects of laser irradiation on the skin," NEREM Record, pp. 152-153, 1965.
Kuhns J.G. et al., "Laser injury in skin," Laboratory Investigation, vol. 17, No. 1, pp. 1-13, Jul. 1967.
Kuizenga, Dirk J. et al., "FM and AM Mode Locing of the Homogenous Laser-Part I: Theory", IEEE Journal of Quantum Electronics, vo. 6, No. 11, Nov. 1970, pp. 694-708.
Lee, Junsu et al., "Q-switched Mode-Locking of an Erbium-doped Fiber Laser through Subharmonic Cavity Modulation", Photonics Conference (IPC), 202 IEEE, Sep. 23, 2012, pp. 664-665.
Leger, J. et al., "Geometrical Transformation of Linear Diode-Laser Arrays for Longitudinal Pumping of Solid-State Lasers", IEEE Journal of Quantum Electronics, vol. 28, No. 4, Apr. 1992.
Lesnik et al., "Agents that cause enlargement of sebaceous glands in hairless mice," Arch. Dermatol., 284:100-105, 1992.
Levin, G. et al., "Designing with hyseretic current-mode control, " EDN Magazine, pp. 1-8, Apr. 11, 1996.
Levin, G. et al., "Designing with hyseretic current-mode control, " EDN Magazine, pp. 1-8, Apr. 28, 1994.
Lucchina et al., "Fluorescence photography in the evaluation of acne," J. Am. Acad. Dermatol. 35:58-63 (1996).
Maegawa, et al., "Effects of Near-Infrared Low-Level Laser Irradiation on Microcirculation," Lasers in Surgery and Medicine, vol. 27, pp. 427-437, 2000.
Mamedova et al., "Microbiological Estimate of Parodontis Laser Therapy Efficiency," SPIE vol. 1984, pp. 247-249.
Mumford, "Effect of Soft Laser Treatment on Wound Healing in the Hamster Oral Mucosa," American Society for Laser Medicine and Surgery, Supp. 8, Abstracts, Abstract 25, 1996.
Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.
Manstein, D., et al., "Fractional Photothermolysis: A New Concept for Cutaneous Remodeling Using Microscopic Patterns of Thermal Injury," Lasers in Surgery and Medicine, 34: 426-438 (2004).
Manuskiatti et al., "Laser hair removal affects sebaceous glands and sebum excretion: A pilot study," J. Am. Acad. Dermatol., 41:176-180, 1999.
Margolis, R.J. et al., "Visible action spectrum for melanin-specific selective photothermolysis," Lasers in Surgery and Medicine, vol. 9, pp. 389-397, 1989.
Marinelli et al., "Diode laser illuminated automotive lamp systems," SPIE Proceedings vol. 3285:170-177 (1998).
Marshak, I.S., et al., "Pulsed Light Sources," State Power Engineering Press, Moscow and Leningrad (1963).
Matsunaga et al., "Effect of pH on Dye-Laser Output Power", J. Appl. Phys. 48(2):842-844 (Feb. 1977).
McCullough, David L., M.D., "Transurethral Laser Treatment of Benign Prostatic Hyperplasia," and "Transurethral Ultrasound-guided Laser-Induced Prostatectomy (TULIP) Procedure): A Canine Prostate Feasibility Study," by Roth, Robert A., M.D., et al., The Journal of Urology, 146:1126-1135 (1991).
McDaniel, et al., "Hexascan: A New Robotized Scanning Laser Handpiece," Cutis, 45:300-305 (1990).
McNicholas, T. A., et al., "Interstitial Laser Coagulation of the Prostate: Experimental Studies," SPIE, 1421:30-35 (1991). (From Proceedings of Lasers in Urol., Laparoscopy, and General Surgery, Jan. 21-23, 1991).
Mingxin, Qiu et al., "Performance of a Nd:YVO4 microchip laser with continuous-wave pumping at wavelengths between 741 and 825 nm", Applied Optics, vol. 32, No. 12, Apr. 20, 1993, p. 2085.
[No Author] BIOPTRON Light Therapy System. Website print-out, accessed Jul. 13, 2006 (2 pages).
[No Author] Derma Chiller advertisement (2 pages) from Paradigm Trex.
[No Author] IPG Data Sheet for TFL Thulium Laser, Jun. 2001.
[No Author] Webpage www.gallery.com—RUTILE (Titanium Oxide)—Retrieved Oct. 3, 2011 from Http://www.galleries.com/minerals/oxides/rutile/rutile.htm. 2 pages.
[No Author] ALTEA Therapeutics—Medicines Made Better (single page website print-out, retrieved Sep. 30, 2004, © 2003-2004).
[No Author] Energy Systems Corporation, "A Practical Guide for the PhotoDem.RTM.VL user," Haifa, Israel, Commercial Brochure 8 Pages, Oct. 1995.
[No Author] "Final Report on the LFDL-10 Laser System for the GCA Corporation," CANDELA Corp., Natick, MA, Section II, subsection 5, pp. 13-15 & 27, Mar. 1982.
[No Author] "Fractional Photothermolysis Redefines Facial Skin Regeneration Science," Aesthetic Buyers Guide, Mar./Apr. 2004, www.miinews.com, pp. 1-4.
[No Author] "Hydrogel Dressings Contain Particles During Laser Therapy," Dermatology Times, ISSN-01966197, p. 26 (1994).
[No Author] "Instruction Manual, TFDL-10," Adapted for SLAC, Candela Corporation, Natick, Oct. 1985.
[No Author] "Lasers Battle for Prostatectomy Market," Medical Laser Industry Report, 5:1-3 (Aug. 1991).
[No Author] "LFDL-8 Instruction Manual," Candela Laser Corporation, Wayland, MA Revised Oct. 1987.
[No Author] "LFDL-8 Instruction Manual," Candela Laser Corporation, Wayland, MA, Jan. 1982, Revised Jun. 1987.

(56) References Cited

OTHER PUBLICATIONS

[No Author] "LFDL-8 Instruction Manual," Cynosure, Inc., Bedford, MA, Revised Nov. 1992.
[No Author] "Prostate Enlargement: Benigh Prostatic Hyperplasia," brochure from U.S. Department of Health and Human Services, pp. 1-14, (at least by 1992).
[No Author] "Special Instruction and Test Results for the LFDL-2 Wave Guide Laser," Candela Laser Corporation, Wayland, MA, Sep. 1982.
[No Author] "The Laser TURP Advantage," INTRA-SONIX, Inc. pp. 1-4 (1991).
[No Author] BECKMAN Laser Institute "Experimental PDT to Prevent Esophagus Cancer," (8 pages) 1996.
[No Author] Cynosure Dioderm 510(k) Notification K992765 for Cynosure, Inc. to Food and Drug Administration, dated: Aug. 16, 1999 and Aug. 20, 1999 (Additional Information).
[No Author] RELIANT Technologies, Inc. "Physicians Guide: Understanding Faxel Laser Treatment," pp. 1-10 (2004).
[No Author] RITTER Sybron Corporation, "Electrosurgery, A Guide for Operating Room Personnel," pp. 1-22, (Jun. 1976).
[No Author] Selective Photothermolysis of Sebaceous Glands, Department of Health and Human Services, Public Health Service, Small Business Innovation Research Program II Grant Application, CYNOSURE, Inc., dated: Jul. 27, 2000, pp. 17-39 and 43-44.
[No Author] "Innovative Non-Surgical Treatment for Barrett's Esophagus", Jul., 1995, see http://www.plsgroup.com/dg950728.htm.
"American Society for Laser Medicine and Surgery Abstracts," Lasers in Surgery and Medicine, Supplement 6, p. 46 (1994).
Anderson, R.R., et al., "Microvasculature Can Be Selectively Damaged Using Dye Lasers: A Basic Theory and Experimental Evidence in Human Skin," Lasers in Surgery and Medicine 1:263-276 (1981).
Altshuler et al., "Human Tooth as an Optical Device," SPIE vol. 1429 Holography and Interferometry and Optical Pattern Recognition in Biomedicine, pp. 95-104, 1991.
Altshuler et al., "Modern Optics and Dentistry," Laser in Dentistry, pp. 283-297, 1995.
Altshuler et al., "New Optical Effects in the Human Hard Tooth Tissues," Lasers and Medicine, Proc. SPIE vol. 1353, pp. 97-102, 1989.
Altshuler, et al., "Self Canalization of Laser Microbeam in Tissue as Fundamental Mechanism of Fractional Skin Resurfacing", Lasers in Surgery and Medicine Supple 15, 21, 2003.
Altshuler, G.B. et al., "Acoustic response of hard dental tissues to pulsed laser action," SPIE, vol. 2080, Dental Application of Lasers, pp. 97-103, 1993.
Altshuler, G.B. et al., "Extended theory of selective photothermolysis," Lasers in Surgery and Medicine, vol. 29, pp. 416-432, 2001.
Amy, R.L. et al., "Selective mitochondrial damage by a ruby laser microbeam: An electron microscopic study," Science, vol. 15, pp. 756-758, Nov. 1965.
Anderson, R.R. et al., "Selective photothermolysis: Precise microsurgery by selective absorption of pulsed radiation," Science, vol. 220, pp. 524-527, Apr. 1983.
Anderson, R.R. et al., "The optics of human skin," Journal of Investigative Dermatology, vol. 77, No. 1, pp. 13-19, 1981.
Ang et al., "Kalman Filtering for Real-Time Orientation Tracking of Handheld . . .", 2004 IEEE/RSJ Iner Conf on Intell Robots and Systems (IROS), Sendai, Japan.
Ang et al., "Design of All-Accelerometer Inertial Measurement Unit for Tremor Sensing in Hand-Held . . .", 2003 IEEE Inter Conf on Robotice and Automation (col. 2), Taipei, Taiwan.
Angelis, et al., "Fractional, Non-Ablative Laser Therapy for the Treatment of Striae Distensae", White Paper published by Palomar Medical Technologies, Inc. (2009)5 pages.
Apfelberg et al. "Analysis of Complications of Argon Laser Treatment for Port Wine Hemangiomas with Reference to Striped Technique," Lasers in Surgery and Medicine, 2:357-371 (1983).
Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).
Apfelberg, D.B., "A Preliminary Study of the Combined Effect of Neodymium:YAG Laser Photocoagulation and Direct Steroid Instillation in the Treatment of Capillary/Cavernous Hemangiomas of Infancy," Department of Plastic Surgery and Comprehensive Laser Center, Palo Alto Medical Foundation, Palo Alto, CA, pp. 94-103 (1989).
Apfelberg, D.B., "Combination Treatment for Massive Cavernous Hemangioma of the Face: YAG Laser Photocoagulation Pulse Direct Steroid Injection Followed by YAG Laser Resection with Sapphire Scalpel Tips, Aided by Superselective Embolization," Lasers in Surgery and Medicine, 10:217-223 (1990).
Belikov, A.V. et al., "Identification of enamel and dentine under tooth laser treatment," SPIE vol. 2623, Progress in Biomedical Optics Europt Series, Proceedings of Medical Applications of Lasers III, pp. 109-116, Sep. 1995.
Benjavitvilai, C. et al., "Fuzzy Calibration of Magnetometer in Presence of Surgical Microscope," 2005 27th Annual International Conference of the IEEE Engineering in Medicine and Biology Society (IEEE Cat. No. 05CH37611C), Shanghai, China, Aug. 31-Sep. 3, 2005.
Bjerring, P. et al., "Selective Non-Ablative Wrinkle Reduction by Laser," J Cutan Laser Ther, vol. 2, pp. 9-15, 2000.
Blankenau et al., "In Vivo Caries-Like Lesion Prevention with Argon Laser: Pilot Study," Journal of Clinical Laser Medicine and Surgery, vol. 17, No. 6, pp. 241-243, 1999.
Bogdan Allemann, et al., "Laser Principles", Physical and Electronic Properties of Lasers, Basics in Dermatological Laser Applications, Curr. Probl. Dermatol, Basel, Karger. Zurich, Switzerland and Miami, Florida. vol. 42, pp. 7-23, 2011, 17 pages.
Bohm et al., "The Pilosebaceous Unit is Part of the Skin Immune System," Dermatology, 196:75-79, 1998.
Boiteux, M., et al., "A Transverse Flow Repetitive Dye Laser," Applied Optics, 9, 514 (1970).
Boulnois, J., "Photophysical Processes in Recent Medical Laser Developments: a Review," Lasers in Medical Science, vol. 1:47-66 (1986).
Brauer, Jeremy A. et al., "Successful and Rapid Treatment of Blue and Green Tattoo Pigment With a Novel Picosecond Laser", Archives of Dermatology, vol. 148, No. 7, 2012, pp. 820-823.
Britt et al., "The Effect of pH or Photobleaching of Organic Laser Dyes", IEEE J. Quantum Electron. (Dec. 1972), 913-914.
Burlamacchi et al, "A Simple Reliable Waveguide Dye Laser for Ophthalmological Applications," Rev of Sci Instrum; vol. 46; No. 3; pp. 281-283, Mar. 1975.
Chan, E.K., "Effects of Compression on Soft Tissue Optical Properties," IEEE Journal of Selected Topics in Quantum Electronics, vol. 2, No. 4, pp. 943-950 (Dec. 1996).
Costello, A. et al., "Nd:YAG Laser Ablation of the Prostate as a Treatment for Benign Prostatic Hypertrophy," Lasers in Surgery and Medicine, 12:121-124 (1992).
Cunliffe, "Acne Vulgaris. The Past, the Present and the Future," Acta Bermatovener (Stockh) Suppl. 120, pp. 34-38, 1985.
Dabrowska, "Intravital Treatment of the Pulp with Stimulation Laser Biostimulation," Abstract Rocz-Akad-Med-Bialymst. 1997; 42(1): 168-76.
Dierickx, C.C. et al., "Thermal Relaxation of Port-wine Stain Vessels Probed In Vivo: The Need for 1-10 Millisecond Laser Pulse Treatment," The Journal for Investigative Dermatology, pp. 709-714 (1995).
Dixon et al. "Hypertrophic Scarring in Argon Laser Treatment of Port-Wine Stains," Plastic and Reconstructive Surgery, 73:771-777 (1984).
Dock et al., "Clinical Histologic and Ultrastructural Evaluation of Solar Elastosis Treated With the Pulsed Dye Laser," American Society for Laser Medicine and Surgery Abstracts, p. 54 (Apr. 1997).
Doukas et al., "Transdermal Drug Delivery With a Pressure Wave," Advanced Drug Delivery Reviews 56 (2004), pp. 559-579.

(56) References Cited

OTHER PUBLICATIONS

Dover J.S. et al., "Pigmented guinea pig skin irradiated with Q-switched ruby laser pulses," Arch Dermatol, vol. 125, pp. 43-49, Jan. 1989.
Dufresne et al., "Squamous cell carcinoma arising from the follicular occlusion triad," J. Am. Acad. Dermatol. 35(3), Part 1:475-477, 1996.
Ellenberger, et al. "Single-Frequency Nd:Glass Laser Oscillator with Pulse-Transmission-Mode Q-Switch with Pulse-Transmission-Mode Q-Switch," Optics communication, vol. 81, No. 6 (Mar. 1991).
Ertan et al., "Esophagel Adenocarcinoma Associated with Barrett's Esophagus: Long-term Management with Laser Ablation", Am. J. Gastro, 90: pp. 2201-2203, 1995.
Fallon Friedlander, "Effective Treatment of Acne Fulminans-Associated Granulation Tissue with the Pulsed Dye Laser," Pediatric Dermatology, 15(5):396-398, 1998.
Finkelstein L.H. et al., "Epilation of hair-bearing urethral grafts using the neodymium:yag surgical laser," Journal of Urology, vol. 146, pp. 840-842, Sep. 1991.
Fiskerstrand E.J. et al., "Hair Removal with Long Pulsed Diode Lasers: A Comparison Between Two Systems with Different Pulse Structures," Lasers in Surgery and Medicine, vol. 32, pp. 399-404, 2003.
Fletcher, A.N et al., "Improving the Output and Lifetime of Flashlamp-Pumped Dye Lasers" Proceedings of the International Conference on Lasers '85, pp. 797-804, Dec. 2-6, 1985.
Forrest-Winchester et al., "The Effect of Infrared Laser Radiation on Dentinal Permeability in vitro," Department of Dentistry, University of Queensland Dental School, pp. 1-8, 1992.
Friedman-Birnbaum et al., "Seborrheic Skin and Acne Vulgaris as Protective Factors against the Development of Basal Cell Epithelioma," Dermatolgica, 183:160-163, 1991.
Furumoto, H., "Dye Chemistry and System Study for Optimum Laser Operation at 436 NM Using the LFDL-10 Laser," Prepared for Burlington Division Geophysical Corporation of America, pp. 1-23, Mar. 1982.
Ginsbach et al. "New Aspects in the Management of Benign Cutameous Tumors," Laser 79 Opto-Electronics, Munich Conference Proceedings, 344-347 (1979).
Goldberg, "Lasers for Facial Rejuvenation", Am J. Clin. Dermatol., 4(4):225-234, 2003, 10 pages.
Goldberg, "Nonablative Resurfacing", Clinics in Plastic Surgery, Skin Laser and Surgery Specialists of New York and New Jersey. Westwood, New Jersey. vol. 27, No. 2, Apr. 2000, 6 pages.
Goldman, L. et al. "Treatment of basal cell epithelioma by laser radiation," JAMA, vol. 189, No. 10, pp. 773-775, 1964.
Goldman, L. et al., "Effect of the laser beam on the skin, III. Exposure of cytological preparations," Journal of Investigative Dermatology, vol. 42, pp. 247-251, 1964.
Goldman, L. et al., "Effect of the laser beam on the skin, Preliminary report" Journal of Investigative Dermatology, vol. 40, pp. 121-122, 1963.
Goldman, L. et al., "Impact of the laser on nevi and melanomas," Archives of Dermatology, vol. 90, pp. 71-75, Jul. 1964.
Goldman, L. et al., "Laser action at the cellular level," JAMA, vol. 198, No. 6, pp. 641-644, Nov. 1966.
Goldman, L. et al., "Laser treatment of tattoos, A preliminary survey of three year's clinical experience," JAMA, vol. 201, No. 11, pp. 841-844, Sep. 1967.
Goldman, L. et al., "Long-term laser exposure of a senile freckle," ArchEnviron Health, vol. 22, pp. 401-403, Mar. 1971.
Goldman, L. et al., "Pathology, Pathology of the effect of the laser beam on the skin," Nature, vol. 197, No. 4870, pp. 912-914, Mar. 1963.
Goldman, L. et al., "Preliminary investigation of fat embolization from pulsed ruby laser impacts of bone," Nature, vol. 221, pp. 361-363, Jan. 1969.
Goldman, L. et al., "Radiation from a Q-switched ruby laser, Effect of repeated impacts of power output of 10 megawatts on a tattoo of man," Journal of Investigative Dermatology, vol. 44, pp. 69-71, 1965.
Goldman, L. et al., "Replica microscopy and scanning electron microscopy of laser impacts on the skin," Journal of Investigative Dermatology, vol. 52, No. 1, pp. 18-24, 1969.
Goldman, L. et al., "The biomedical aspects of lasers," JAMA, vol. 188, No. 3, pp. 302-306, Apr. 1964.
Goldman, L. et al., "The effect of repeated exposures to laser beams," Acta derm.-vernereol., vol. 44, pp. 264-268, 1964.
Goldman, L., "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.
Goldman, L., "Effects of new laser systems on the skin," Arch Dermatol., vol. 108, pp. 385-390, Sep. 1973.
Goldman, L., "Laser surgery for skin cancer," New York State Journal of Medicine, pp. 1897-1900, Oct. 1977.
Goldman, L., "Surgery by laser for malignant melanoma," J. Dermatol. Surg. Oncol., vol. 5, No. 2, pp. 141-144, Feb. 1979.
Goldman, L., "The skin," Arch Environ Health, vol. 18, pp. 434-436, Mar. 1969.
Goldman, L., Biomedical Aspects of the Laser, Springer-Verlag New York Inc., publishers, Chapts. 1, 2 & 23, 1967.
Goldman, M. P., "Leg Veins and Lasers," American Society for Laser Medicine and Surgery Abstracts, Fourteen Annual Meeting, Toronto, Ontario, Canada, p. 48 (Apr. 8-10, 1994).
Goldman, M.P., "Sclerotherapy—Treatment of Varicose and Telangiectatic Leg Veins," Second Edition, Mosby, pp. 454-467 (1995).
Gottlieb, I., "Power Supplies, Switching Regulators, Inverters & Converters," 1976.
Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).
Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.
Grossman, M.C. et al., "Damage to hair follicles by normal-mode ruby laser pulses," Journal of the American Academy of Dermatology, vol. 35, No. 6, pp. 889-894, Dec. 1996.
Grossman, M.C. et al., "Laser Targeted at Hair Follicles, " Lasers Med Surg., Suppl. 13:221 (2001).
Tarasov, L. V., Laser Physics, Translated from Russion by Ram S. Wadhwa, MIR publishers, Moscow, pp. 178-181, Chapter 2, 1983.
Tarijian, et al., "Fractional abalative laser skin resurfacing: A review", Journal of Cosmetic and Laser Therapy, 13:262-264, ISSN 1476/4172. Informa UK Ltd. Sep. 2011, 3 pages.
Taylor, C.R. et al., "Treatment of tattoos by Q-switched ruby laser," Arch. Dermatol. vol. 126, pp. 893-899, Jul. 1990.
Togatov, V.V. et al., "Electronic discharge module for pump systems of solid-state lasers", Optical Journal, V. 67, n. 4, pp. 92-96 (2000).
Tuchin, V.V., "Laser light scattering in biomedical diagnostics and therapy," Journal of Laser Applications, vol. 5, No. 2-3, pp. 43-60, 1993.
Unger, W.P., Laser hair transplantation III: Computer-assisted laser transplanting. Dermatol Surg. 1995; 21:1047-1055.
Van Bruegel, "Power Density and Exposure Time of He-Ne Irradiation Are More Important Than Total Energy Dose in Photo-Biomodulation of Human Fibroblasts in Vitro," Lasers in Surgery and Medicine, vol. 12 pp. 528-537, 1992.
Vasily, et al., "Non-Ablative Fractional Resurfacing of Surgical and Post-Traumatic Scars", Journal of Drugs in Dermatology, 8(11):998-1005, Nov. 2009, 8 pages.
Walsh, "Laser "Curettage": a Critical Analysis, " Periodontology 14:4-12, 1993.
Walsh, "The Current Status of Low Level Laser Therapy in Dentistry. Part 1. Soft Tissue Applications," Aust. Dent. J. Aug. 1997;42(4):247-54.

(56) References Cited

OTHER PUBLICATIONS

Watanabe, S. et al., "Comparative studies of femtosecond to microsecond laser pulses on selective pigmented cell injury in skin," Photochemistry and Photobiology, vol. 53, No. 6, pp. 757-762, 1991.
Watanabe, S. et al., "The Effect of Pulse Duration on Selective Pigmented Cell Injury by Dye Lasers," The Journal of Investigative Dermatology, 88:523, 1987.
Watson, G. M., MS, "Minimally Invasive Therapies of the Prostate," Minimally Invasive Therapy, 1:231-240 (1992).
Wei Tech Ang et al., "Design of All-Accelerometer Inertial Measurement Unit for Tremor Sensing in Hand-Held Microsurgical Instrument," 2003 IEEE International Conference on Robotics and Automation (vol. 2), Taipei, Taiwan, Sep. 14-19, 2003.
Wei Tech Ang et al., "Kalman Filtering for Real-Time Orientation Tracking of Handheld Microsurgical Instrument," 2004 IEEE/RSJ International Conference on Intelligent Robots and Systems (IROS), Sendai, Japan, Sep. 28-Oct. 2, 2004.
Welch, A.J. et al., "Evaluation of cooling techniques for the protection of the epidermis during HD-yag laser iradiation of the skin," Neodymium-Yag Laser in Medicine and Surgery, Elsevier Science Publishing Co., publisher, pp. 195-204, 1983.
Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.
Wilson, S.W., "Passive Alignment of a Semiconductor Laser to an Optical Fiber," University of Maryland, Master's Thesis (1995).
Winters, B.H. et al., "Photochemical Products in Coumarin Laser Dyes," Appl. Phys. Lett. 25:723-724 (1974).
Yang et al., "Hybrid optoelectronics: A polymer laser pumped by a nitride light emitting diode," Applied Physics Letters 92, Jan. 23, 2008.
Yules, R.B. et al., "The effect of Q-switched ruby laser radiation on dermal tattoo pigment in man," Arch Surg, vol. 95, pp. 179-180, Aug. 1967.
Zapka et al. "Pulse Slicing and Pockels Cell Shutters," J. Phys. E: Sci, Instrum., vol. 15 (1982).
Zayhowski, J.J. et al., "Gain-switched pulsed operation of microchip lasers", Optice Letters, Optical Society of America, US 14:23, Dec. 1, 1989, pp. 1318-1320.
Zeitler, E. et al., "Laser Characteristics that Might be Useful in Biology," Laser Applications in Medicine and Biology, vol. I, M.L. Wolbarsht, editor, Plenum Press, publishers, Chapter 1, pp. 1-18, 1971.
Zonios et al., "Skin Melanin, Hemoglobin, and Light Scattering Properties can be Quantitatively Assessed in Vivo Using Diffuse Reflectance Spectroscopy," Journal of Investigative Dermatology, 117:1452-1457 (Dec. 2001).
Bastien St-Louis Lalonde et al., "Visible and near infrared resonance plasmonic enhanced nanosecond laser Uploporalion of cancer cells", Biomedical Optics Express4:4, Apr. 1, 2013, pp. 490-499.
Datta, "Tissue Surgery and Subcellular Pholodisruption with Femlosecond Laser Pulses", Senior thesis presented to The Department of Physics at Harvard University, Cambridge, Massachusetts, May 2001 (81 pages).
Hellman et al., "Biophysical Response to Pulsed Laser Microbeam-Induced Cell Lysis and Molecular Delivery", J Biopholonics, 1(1): Mar. 2008, pp. 24-35.
Karpiouk et al., "Quantitative ultrasound method to detect and monitor laser-induced cavitation bubbles", J Biomed : Opt. 2008; 13(3), pp. 1-24.
Philipp et al., "Cavitation erosion by single laser-produced bubbles", J. Fluid Mech. (1998) vol. 361, pp. 75-116.
Schaffer, "Interaction of Femlosecond Laser Pulses with Transparent Materials", thesis presented to The Department of Physics at Harvard University, Cambridge, Massachusetts, May 2001 (193 pages).
Sharei et al., "Plasma membrane recovery kinetics of a microfluidic intracellular delivery pallform", Integr. Biol., 2014, 6, pp. 470-475.
Vogel et al., "Shock wave emission and cavitation bubble generation by pocosecond and nanosecond optical breakdown in water", J. Acoust. Soc. Am. 100 (1), Jul. 1996, pp. 148-165.
Doukas et al., Physical Characteristics and Biological Effects of Laser-Induced Stress Waves, Ultrasound in Med. & Biol., No. 2, pp. 151-164 (1996).
Brujan et al., "Stress wave emission and cavitation bubble dynamics by nanosecond optical breakdown in a tissue phantom", Journal of Fluid Mechanics, Jul. 2006, pp. 281-308.
Aglyamov et al., "ultrasound measurements of cavitation bubble radius for femtosecond laser-induced breakdown in , water", Opt. Lett. Jun. 15, 2008; 33(12): 8 pages.
Lukianova-Hleb et al., "Generation and detection of plasmonic nanobubbles in zebrafish", Nanotechnology, Jun. 4, 2010; 21(22): pp. 1-22.
Lapotko, "Optical excitation and detection of vapor bubbles around plasmonic nanoparticles", Optics Express 17:4, Feb. 16, 2009, pp. 2538-2556.
Vogel et al., "Mechanisms of Pulsed Laser Ablation of Biological Tissues", Chem. Rev. 2003. 103, pp. 577-644.
Kitz et al., "Vapor bubble generation around gold nanoparticles and its application to damaging of cells", Biomedical Optics Express, 2:2, Feb. 1, 2011, pp. 291-304.
Karpiouk et al., "Development of ultrasound technique to detect and characterize laser-induced microbubbles", Proc. of SPIE, vol. 6435 (2007), 9 pages.
Lauterborn et al., "Shock Wave Emission by Laser Generated Bubbles", Bubble Dynamics & Shock Waves, Shockwaves 8, pp. 67-103 (2013).
Peeters et al., "Mechanisms of nanoparticle-mediated photomechanical cell damage", Biomedical Optics Express, 3:3, Mar. 1, 2012, pp. 435-446.
Zysset et al., "Picosecond Optical Breakdown: Tissue Effects and Reduction of Collateral Damage", Lasers in surgery and Medicine 9 (1989) pp. 193-204.
Pozar et al., "Optical Measurements of the laser-induced ultrasonic waves on moving objects", Optics Express 17:25, Dec. 7, 2009, pp. 22906-22911.
Sharei et al., "A vector-free microfluidic platform for intracellular delivery", PNAS, 6:110, Feb. 5, 2013, pp. 2082-2087.
Lu et al., "Regulation of HMGB1 release by inflammasomes", Protein Cells 2013, 4(3); pp. 163-167.
Srikrishna et al., "Endogenous Damage-Associated Molecular Pattern Molecules at the Crossroads of Inflammation and Cancer", Neoplasia 11:7, Jul. 2009, pp. 615-628.
Letfullin et al., "Laser-induced explosion of gold nanoparticles: potential role for nanophotpthermolysis of cancer", Nanomedicine (2006) 1(4), pp. 473-480.
Translation of Search Report from the Federal Institute of Industrial property for Russian Federation Patent Application No. 2022132377; dated Aug. 22, 2024; (2 pages).
Miccoli et al., "High-Denisty Electrical Recording and Impedance Imaging With a Multi-Modal CMOS Multi-Electrode Array Chip"; Frontiers in Neuroscience; Jun. 25, 2019; vol. 13; Article 641; (14 pages).
Laeseke et al.; "Multiple-electrode radiofrequency ablation: simultaneous production of separate zones of coagulation in an in vivo porcine liver model"; J. Vasc. Interv. Radiol.; Dec. 2005; 16(12): 1727-35; (2 pages).
Trelles et al.; "Transepidermal delivery of cosmeceuticals using radiofrequency and ultrasound: Study of the penetration of a cosmetic gel in vivo by fluorescence microscopy"; Global Dermatology; 2015; vol. 2(3); pp. 143-146.
Goel et al.; "Use of nanofractional radiofrequency for the treatment of acne scars in Indian skin"; J Cosmet Dermatol.; Jun. 2017; 16; pp. 186-192.
Written Opinion for Singapore Application No. 11202254801S, dated Nov. 8, 2025, (7 pages).

* cited by examiner

Push to release disposable
(both sides)
38
7
10
3
30
25

10
7
5
5a
5b
5c
5d 3
3a
38
10
25
30

3
3a
10
35
25
30

Pins contact skin 5a
5b
5c
5d
Fractional Probe Pins
Skin
RF energy is pulsed

Skin / tissue transformation
Fractional Probe Pins
Skin
RF energy transforms the epidermis and electrode pins penetrate the epidermis Fractional Probe Pins
Skin

- Before energy 3017Ω, 67mArms, 203Vrms
- After energy 1417Ω, 277mArms, 393Vrms
- Impedance change within ~600us of ramp start

- Fractional penetration and impedance drop seen

SYSTEM AND METHOD FOR SKIN REJUVENATION USING IMPEDANCE MONITORING

CROSS REFERENCE TO RELATED APPLICATIONS

This application claims priority to and the benefit of U.S. Provisional Patent Application No. 63/024,483 entitled "System and Method for Skin Rejuvenation Using Impedance Monitoring" filed on May 13, 2020, the disclosure of which is herein incorporated by reference in its entirety.

FIELD

The present disclosure relates generally to systems and methods for treating a patient's skin (e.g., dermis and hypodermis) and other target tissue with radiofrequency (RF) energy.

BACKGROUND

Electrosurgical devices are known for applying RF energy to tissue so as to generate a variety of effects, including invasive procedures (e.g., for ablating or vaporizing tissue) or less-invasive procedures (e.g., to gently heat the surface of the skin). However, a need remains for improved methods and system for providing RF energy in cosmetic and/or aesthetic applications, for example, in order to improve the appearance of skin so that it is (or appears) tightened/smoothed.

SUMMARY

In various embodiments, the disclosure relates to systems and methods for treating tissue. A treatment device is activated and RF energy is delivered to tissue through one or more electrodes. Monitoring impedance during one or more time periods relative to treatment, such as during pre-treatment, treatment, and post-treatment, and subsets of the foregoing is performed. Impedance monitoring is performed during a period of impedance values increasing, which is correlated with tissue transformation, such as tissue removal. Impedance monitoring is performed during a period of time when impedance drops. The impedance drop after starting treatment is correlated with one or more electrodes transmitting a signal indicative of an impedance drop as a result of contacting another region or volume of tissue having different properties relative to the transformed tissue such as a previously uncontacted layer of hydrated tissue or tissue having another property correlated with lower impedance, lower resistances, or increased electrical conductance. In various embodiments, the treatment is stopped, such as by stopping delivery of RF energy, after a treatment time period measured from when the foregoing impedance drop is measured or detected.

In part, the disclosure relates to a method of cosmetic tissue treatment. The method includes disposing a treatment applicator that includes an electrode array comprising a plurality of needles on a portion of tissue such that a region of the electrode array contacts the portion of tissue, wherein each needle is an electrode in electrical communication with a control system; applying a pulse of radio frequency (RF) energy to the portion of tissue through the electrode array; measuring impedance of electrode array over time; detecting a drop in the measured impedance while electrode array is in contact with the portion of tissue; and upon detection of the reduction in impedance by a threshold value, terminating application of the pulse of RF energy after a treatment time period.

In one embodiment, the duration of the pulse is between about 1 ms and about 12 ms. In one embodiment, impedance is measured at a sampling rate that ranges from about 10 KHz to about 50 KHz. In one embodiment, impedance is measured at a sampling rate of about 30 KHz. In one embodiment, the method further includes avoiding initiating muscle twitches during treatment time period and optionally the electrode array has an output voltage with a ramp time ranging from about 100 microseconds to about 5 ms. In one embodiment, the plurality of electrodes is connected in parallel. In one embodiment, the method includes transforming tissue such that tissue is removed in vicinity of contact with a subset of the plurality of electrodes. In one embodiment, the method further includes applying a topical on the portion of the tissue prior to disposing the treatment applicator. In one embodiment, the method further includes applying a topical on the portion of the tissue after the treatment time period. In one embodiment, the method further includes applying a topical on the portion of the tissue before and after the treatment time period. In one embodiment, the topical is a skin moisturizer. In one embodiment, the pulse of RF energy travels along surface of electrode and initiates a tissue effect when delivered to the portion of the tissue. In one embodiment, one or more annular injuries is generated in tissue in response to pulse of radio frequency (RF) energy.

In part, the disclosure relates to an apparatus for treating tissue. The apparatus includes a first treatment applicator head including a first plurality of needles; and an applicator body having a first end connected to the first treatment applicator head; wherein the applicator body includes a second end in communication with a radio frequency (RF) power source and a control system; wherein the first treatment applicator head, when connected to the applicator body, is electrically connected with the RF power source in communication with the second end; wherein the control system is operable to terminate tissue treatment after a treatment period occurs, the treatment period initiated upon detection of a drop in impedance following an initial increase in impedance. In one embodiment, each needle of the plurality of needles has a blunt tip. In one embodiment, the apparatus further includes a second treatment applicator head including a second plurality of needles, the first end of the applicator body connected to the second treatment applicator head, wherein the second treatment applicator head, when connected to the applicator body, is electrically connected with the RF power source.

In part, the disclosure relates to a method of treating tissue and the method includes applying radio frequency (RF) power to tissue through a plurality of electrodes; during the application of the RF power, periodically measuring impedance of the tissue; and controlling the application of RF power based on the impedance of the tissue such that treatment terminates after the measurement of a decrease in measured impedance. In one embodiment, the decrease in measured impedance is correlated with one or more of the plurality of electrodes contacting an untreated region of tissue. In one embodiment, a first conductive property of the untreated region of tissue differs from a second conductive property of a treated region of tissue. In one embodiment, the treated region of tissue is disposed above the untreated region of tissue. In one embodiment, RF power is reduced upon detection of a decrease in impedance of the tissue. In one embodiment, the RF power is applied for a treatment time that ranges from about 1 ms and about 12 ms. In one embodiment, the decrease in measured impedance ranges from about 10% to about 90%. In one embodiment, the decrease in measured impedance ranges from about 20% to about 50%.

Although, the disclosure relates to different aspects and embodiments, it is understood that the different aspects and embodiments disclosed herein can be integrated, combined, or used together as a combination system, or in part, as separate components, devices, and systems, as appropriate. Thus, each embodiment disclosed herein can be incorporated in each of the aspects to varying degrees as appropriate for a given implementation. Further, the various systems, probes, applicators, needle arrays, controllers, components and parts of the foregoing can be used with any suitable tissue surface, cosmetic applications, and medical applications and other methods and conjunction with other devices and systems without limitation.

These and other features of the applicant's teachings are set forth herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

Unless specified otherwise, the accompanying drawings illustrate aspects of the innovations described herein. Referring to the drawings, wherein like numerals refer to like parts throughout the several views and this specification, several embodiments of presently disclosed principles are illustrated by way of example, and not by way of limitation. The drawings are not intended to be to scale.

DETAILED DESCRIPTION

In part, the disclosure relates to systems, devices, and methods of directing and/or delivering electromagnetic energy such as radio frequency (RF) energy to one or more tissue regions, volumes, or layers to transform the foregoing tissue by one or more mechanisms of action such that cosmetic, rejuvenating, and/or other tissue changes directly or indirectly result or are initiated. Examples of other tissue changes or transformations of the tissue that may be caused or initiated using the applicators and methods disclosed herein may include stimulating, repairing and/or growing the tissue or one or more components thereof such as through fractional rejuvenation or other mechanisms. In one embodiment, RF treatment transforms the tissue by increasing collagen production. The treatment applicators may also be referred to as probes or RF treatment devices and as otherwise referenced herein.

Without being held to a particular theory or mechanisms, the application of the pin/needle-based electrode arrays may transform the tissue using electrical signals as opposed to optical signals such as laser light. Specific types of tissue transformations and effects generated or initiated relative to tissue during a given treatment session may include, without limitation, ablation, tissue removal, cauterization, plasma generation, RF induced plasma generation, non-thermal RF induced pressure waves, tissue charring, tissue vaporizing, mechanical changes to tissue, lesion formation, void formation, tissue excavating, increase production of tissue compounds, tissue scarring, and combinations thereof. A given tissue transformation is customized on a per user basis using a treatment time that is regulated by monitoring impedance changes.

Figure 1A:
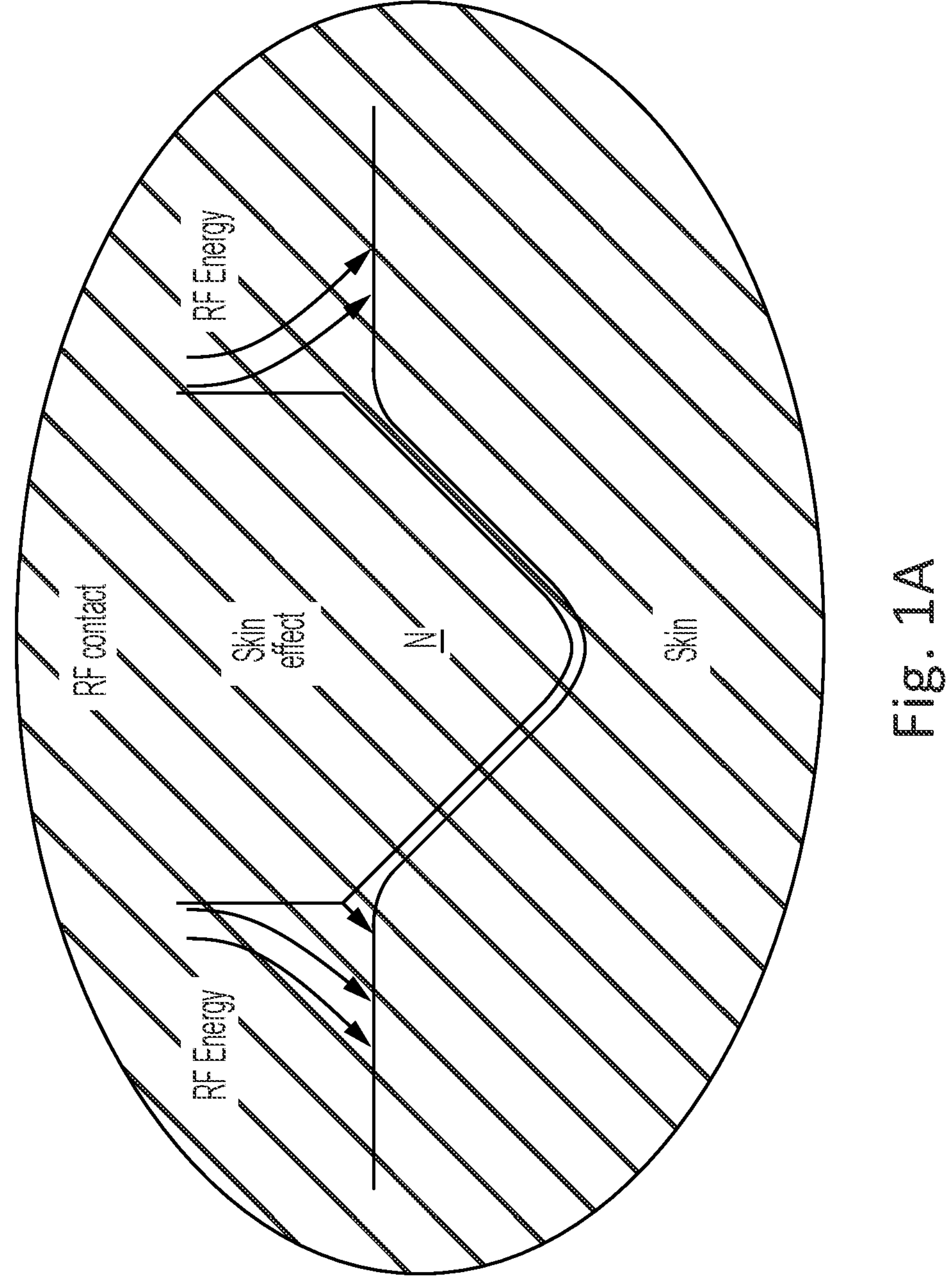
FIG. 1A is a diagram showing an RF non-penetrating needle/electrode in contact with tissue in accordance with an embodiment of the disclosure.

FIG. 1A shows an RF tissue contacting non-penetrating needle/electrode N pushed against a tissue surface such as skin. The RF energy from the outer surface of the needle/electrode N travels along the outer surface of the needle/electrode N and makes contact with the surface of the tissue.

FIG. 1A shows how the outer surface of the needle/electrode N and the RF delivered thereby initiates an electrical skin effect in one or more regions near or in contact with the electrode. The electrical skin effect is the tendency of an alternating electric current (AC) to become distributed within a conductor such that the current density is largest near the surface of the conductor and decreases exponentially with greater depths in the conductor. The electric current flows mainly at the "skin" of the conductor, between the outer surface and a level called the electrical skin depth. Electrical skin depth depends on the frequency of the alternating current; as frequency increases, current flow moves to the surface, resulting in less electrical skin depth. Referring still to FIG. 1A, in particular, the electrical skin effect is initiated as a result of the tendency of an alternating electric current (AC) to become distributed within a conductor such that the current density is largest near the surface of the conductor and decreases exponentially with greater depths in the conductor. The conductor surface corresponds to the surface of the needle/electrode N in various embodiments. This electrical skin effect phenomenon is proportional to the frequency of the AC. In one embodiment, the needle/electrode N receives RF generated using AC generator that has a frequency that ranges from about 0.5 MHz to about 4 MHz. In various embodiments, the selection of the foregoing high frequency range increases the intensity of the electrical skin effect generated by the needle/electrode N. The electrical skin effect imparts a tissue effect in the skin surface (e.g., the superficial skin region)

When such contact, as is shown in FIG. 1A, is established with one or more non-penetrating needle/electrodes N pushed up against or otherwise biased towards or into the skin, there is a tendency for RF energy to meet the surface of the tissue first. Upon the meeting of the RF energy with the surface of the skin tissue, an injury forms around the outer surface of the needle/electrode N. In various embodiments, this injury occurs at the meeting point of the RF energy with the skin surface. The resulting skin effect injury is initially concentrated about the junction of the outer surface of the needle/electrode N and the skin surface.

Figure 1B:
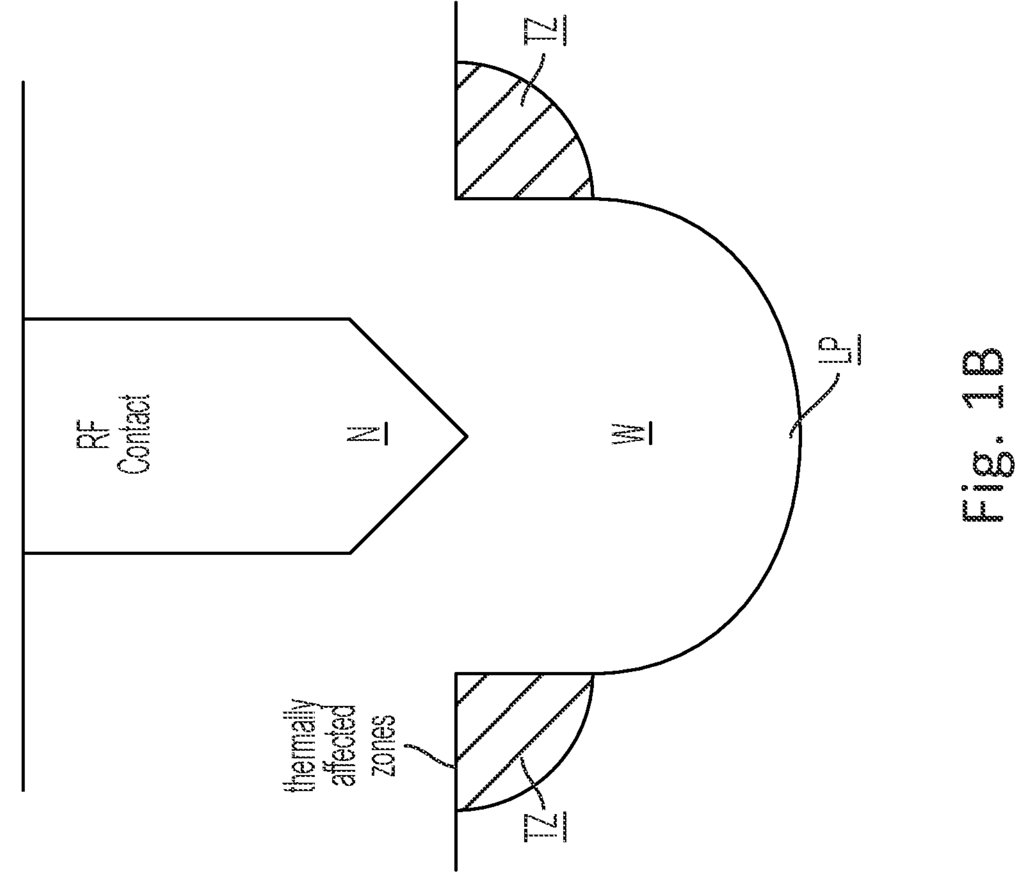
FIG. 1B is a diagram showing annular injury formation and an associated RF electrode/needle pin after delivering RF energy in accordance with an embodiment of the disclosure.

Turning to FIG. 1B, in an embodiment where the needle/electrode N has a circular cross section, an annular type of injury (shown in FIG. 1B) may be created on the skin/tissue surface. The annular injury caused by such a needle/electrode N results in response to concentration of RF energy at the junction points of the outer surface of the needle/electrode N and the skin surface. The injury is annular in geometry, at least in part, because the tip of the non-penetrating needle/electrode N vaporizes and/or ablates the surface of the tissue in contact therewith. The tip of needle/electrode N effectively serves as an RF focus for RF energy along the surface of the needle/electrode N. The RF energy propagates to the adjacent tissue surface wherein one or more tissue injuries are created.

As shown in FIG. 1B, a region of the bottom or low point LP of the well/crater W exposes the dermal or epidermal/dermal junction as a result of the tissue injury generated in response to RF delivery through the needle/electrode N. One or more thermally affected zones TZ may also result from the delivery of RF energy and the associated skin effect by which RF energy travels along surface of conducting needle/electrode N before propagating from point-like tip of needle/electrode N through tissue to reach low point. LP Ablation of the tissue in contact with the tip of the non-penetrating needle/electrode N creates a well (or crater or depression) W in the tissue. Further, the surface of the well or crater W created by the electrode N is ablated/vaporized. This ablation/vaporization exposes the tissue beneath the surface, e.g., dermal tissue and/or epidermal/dermal junction tissue while contributing or causing the appearance of a well or crater W. The exposed tissue about the bottom of the crater W is relatively undamaged (e.g., having minimal thermal effect). The RF treatment using the electrode N effectively reveals one or more portions of tissue by the ablation and/or vaporization of the tissue formerly covering the exposed tissue. The newly exposed tissue may absorb and/or retain topical treatment.

In various embodiments, a topical cream or other medicament may be applied to tissue revealed or exposed as a result of delivery of RF energy as described herein. Various topicals suitable for application to revealed or exposed tissue are discussed in detail herein. For example, certain topicals (e.g., hydrophilic, hydrophobic) might be preferentially employed for the injury provided by the RF treatment non-penetrating needle electrodes N shown in FIG. 1B. Certain topical materials are expected to experience improved uptake and/or retention with the injury shown in FIG. 1B and others disclosed herein. As discussed herein the choice of fundamental frequency can determine the extent of thermal effect in a treatment area such that the electrical skin effect can be exploited by higher fundamental frequencies (e.g., from about 1 kHz to about 1 GHz). Conversely, uniform thermal effect can be achieved with relatively lower fundamental frequencies (e.g., from about 100 Hz to about 1 kHz).

Typically, skin rejuvenation treatments use laser ablation, which can be a complex and costly treatment. Generally, RF treatments are advantageous in terms of reduced costs and less fragile or more easily sourced components. Unfortunately, various methods of applying RF energy have various drawbacks. For example, attempts to use long duration pulses of low RF energy have been used in some treatment systems. Long duration pulses of low RF energy result in higher residual heat retention in the skin. Generally, managing the residual heat is difficult as every individual's skin is different and excess heat results in pain and unpredictable outcomes.

The amount of RF energy required to treat various individuals depends on a multitude of variables (e.g., amount of pigmentation and hydration level of an individual's skin). To help meet some of these technical challenges, the systems and methods disclosed herein have been tailored to provide a cost efficient and customized and user specific method of rejuvenating the skin or otherwise treating a tissue of an individual. In part, the subject specific nature of the treatment may be achieved by incorporating impedance monitoring as a mechanism to customize the treatment times on a per individual basis.

In various embodiments, the disclosure describes a system including a control and/or analysis system connected to a treatment applicator. The control and/or analysis treatment system includes one or more ASICs, circuits, microprocessors or other control systems that stop the delivery of RF energy after an impedance value or threshold or impedance transition is detected/measured and/or after a predetermined period of time after such a detection.

In various embodiments, the treatment applicator includes a treatment applicator head having a set of electrodes arranged in a pattern. The treatment head may be removable/releasable relative to a probe/applicator body. The electrodes are conductive pins or needles or other protuberances that extend from a conductive surface or are otherwise in electrical communication with an analysis and control treatment system. In some embodiments, the electrodes of the treatment applicator are arranged in pattern such as a regular polygon or other shape with electrodes at vertices thereof and/or centrally disposed with regard to such a polygon or other shape. For example, in an embodiment, a treatment applicator includes about 50 electrodes or applicator needles where the electrodes are arranged in rows of about 10 electrodes. In this embodiment, the electrodes are evenly spaced within a tissue-contacting region of the treatment applicator.

Figure 1C:
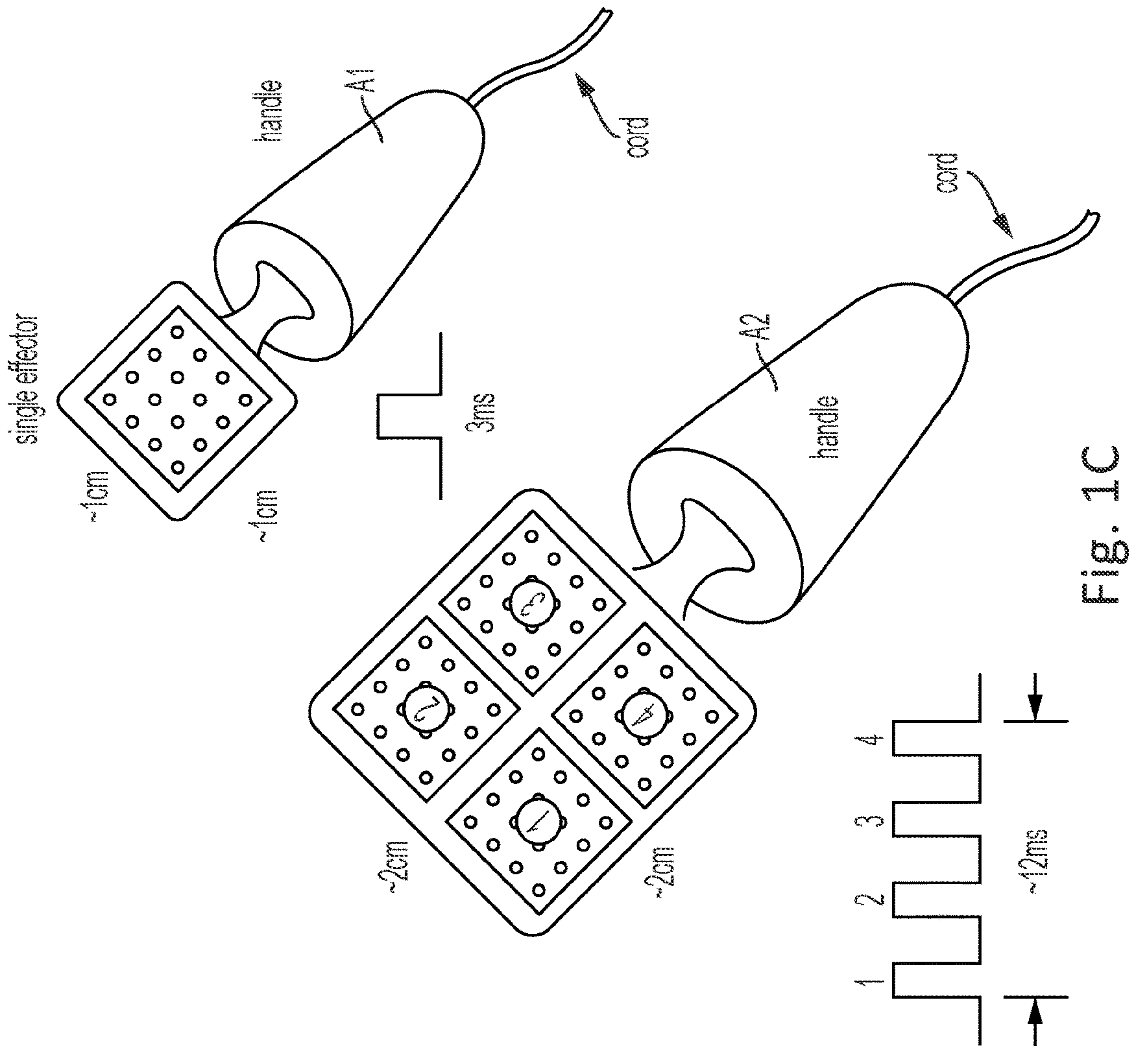
FIG. 1C is a diagram showing a first applicator and a second applicator with different electrode array configurations in accordance with an embodiment of the disclosure.

FIG. 1C shows two different applicators A1, A2. The first applicator A1 has a single array of non-penetrating needle electrodes (e.g., pins). A given array may be supported by or connected to a first applicator head. In one embodiment, the single array of applicator A1 has an area of about 1 cm×about 1 cm. Various applicator embodiments may have two or more applicator heads. The second applicator A2 has four separate about 1 cm×about 1 cm arrays positioned as four corners of a square or rectangle on an applicator surface such that the overall coverage of the pins is about 2 cm×about 2 cm. Each array or combination of arrays may be part of one or more applicator heads that are connected to an applicator body. Multiple applicators may also be used in different embodiments.

In various embodiments, the number of non-penetrating needle electrodes (e.g., pins) in any array and/or in any applicator is limited by distribution of the number of pins in each array in order to maintain uniformity of the energy deposition of each needle. When the number of pins in an array exceeds this allowable threshold, the desired uniformity of treatment degrades such that energy concentration will be unevenly distributed. Factors that determine what the allowable threshold for number of pins in an array is in a given applicator varies. These factors may include diameter of the needles, pitch between adjacent needles, needle material, frequency, mode (whether bipolar or monopolar), time etc. Each applicator A1, A2 includes a handle, an effector, and a cord whether with one array or a plurality of arrays. Each cord connects its applicator to an RF generator and one or more control systems.

When multiple arrays are employed, the arrays need not be activated simultaneously, but can also be activated in a timed sequence in order that the same power source be portioned to the individual smaller array units in a short sequence representing one activation of the RF handpiece. When the array has made contact, a single activation created by for example a footswitch, handswitch or automatically by contact sensing of the pins to the tissue through impedance monitoring, each array can be pulsed to represent one pulse covering an area greater than one individual array. Since the pulse duration is on the order of several milliseconds, and the timing between pulses can be less than a millisecond, a device could theoretically cover many square centimeters with one pulse activation and still be considered a short pulse (<about 100 ms) suitable for a manual stamping technique. In one embodiment, the array of applicator A1 may be energized using RF pulses of about 3 ms in duration. In one embodiment, the array of applicator A2 may be energized using RF pulses of about 3 ms in duration either simultaneously or pursuant to an alternating pattern such as a round robin scheme. In one embodiment, the applicator A2 has a total period of energization of about 12 ms with each of the four arrays being energized for about 4 ms each.

Applicator Array Selection for Treatment Area

The applicator array may be configured to conform to the surface curvature shape of the treatment area. An applicator with conformal surface shape would be beneficial in that it could apply uniform electrode pressure on the underlying skin. The uniform electrode pressure of a conformal applicator is expected to lead to more consistent and more predictable treatment results. Each array element could be rigid, but also employ a suspension to accurately stay normal to a curved tissue plane. An example of such a mechanism can be seen in an electric shaver where each cutting head conforms to the tissue surface through a spring-loaded suspension mechanism. Various array shapes may be envisioned that fit specific anatomical regions, for example around the nose; the upper lip etc.

Configurations of Rows and Columns

In various embodiments, the delivery electrodes may be positioned on a hexagonal or a rectangular grid. A hexagonal arrangement offers the advantage for most uniform distance between an electrode and its nearest neighbors and corresponding uniformity of the biological effect from the treatment. Alternatively, in various embodiments a non-uniform spacing between the delivery electrodes may be beneficial if the desired biological effect has a preferential orientation. For example, for a skin tightening treatment it may be beneficial to have a higher delivery electrodes density in the desired tightening direction and lower density in the transverse direction so that the tissue heating and the healing time is optimized for directional maximum tightening effect with minimal heling time and minimal side effects.

Cross Section of the Pins

The cross section of the individual pins, or delivery electrodes, may be any geometrical shape that leads to blunt tip of the pins pressed against the skin. The blunt tip is preferable so that when the tip array is pressed against the skin there is no pin penetration in the epidermis before RF energy delivery. That arrangement optimizes high RF power density delivery in the epidermis and lower RF power density delivery in the dermis. The area of the skin surface contact of the blunt tip is optimized for sufficiently high RF power density delivery for initiation of the tissue effects and impedance changes described in the present application.

Application of Topicals Before/after Treatment with the Applicators

Topical preparations may be applied to the skin before and/or after RF power delivery. The effect of topical preparations that affect the impedance of the delivery electrodes and/or the underlying skin region have to be evaluated for each specific topical preparation if it is considered for application before RF power delivery. Topical preparations that may undergo chemical, physical or structural changes during RF power delivery have to be evaluated for each specific topical preparation if it is considered for application before RF power delivery. There are no impedance or RF heating considerations for topical preparations applied to the skin after RF power delivery. In some embodiments, topical preparations may be applied to the skin by the RF treatment applicator in predetermined dosage before and/or after RF power delivery.

Applicator Treatment Regime/Timing

A treatment course may be envisioned of a first treatment optionally followed up by multiple treatments at a treatment interval between about 1 week and about 3 months. Multiple treatments with a relatively lower RF power level and/or shorter power delivery on-time would be preferentially delivered at shorter treatment intervals, for example about 1 to about 3 weeks. Multiple treatments with a relatively higher RF power level and/or longer power delivery on-time would be preferentially delivered at longer treatment intervals, for example about 3 weeks to about 3 months. A treatment course may also be employed where the RF power level and/or power delivery on-time is maintained for each follow up treatment in the course of the subject's treatment regime.

A treatment applicator is capable of causing a transformation of the tissue such as lesions or voids relative to a tissue such as the epidermis, for example, in a pattern that spans a region of treatment on or in the subject. Tissue is removed from a region or volume in the vicinity of where contact is made with one or more surfaces of a given pin or needle of the applicator. Each of the lesions is created by a corresponding electrode within a pattern of electrodes within a treatment applicator. Each electrode receives a short burst of high RF energy from a controller and/or analysis system. The lesions are spaced such that each lesion is surrounded by uninjured tissue.

In these instances, the uninjured tissue helps support the repair of the neighboring portions of injured tissue, which facilitates faster healing and/or repair of the injured portions of tissue. In various embodiments, the fractional pattern can be changed to cover varying sizes of treatment areas. In some embodiments, a treatment applicator can cover multiple treatment areas. In these embodiments, one or more of the multiple treatment areas can be treated simultaneously or in sequence to efficiently treat larger portions of skin. Multiple applicators or pads that include pin/needle arrays may also be used.

In various embodiments, a treatment applicator creates a fractional pattern of lesions. For example, a given lesion may range from about 100 microns wide to about 300 microns wide. Similarly, a given lesion may range from about 50 microns deep to about 300 microns in depth. However, in other embodiments, the size of each lesion can be adjusted in response to by a level or duration of power applied through each electrode. The depth and widths ranges above can be expanded or contracted by factors ranging from about 0.1 to about 10. For a given treatment session, RF power and/or duration can be varied to augment the size and/or depth of the lesions as needed. In some instances, the treatment applicator may be used for creating larger lesions, deeper channels, or different sized lesions. In some embodiments, the size and/or shape of each electrode can be changed to select and/or adjust the size and/or depth of lesions created. In a given treatment session, in addition to RF energy delivery, an operator of treatment system may apply downward pressure to push the needle/pin array into the tissue under treatment.

In various embodiments, a treatment applicator includes one or more sensors to detect various changes within the skin during treatment. For example, in one embodiment, a treatment applicator includes an impedance sensor for detecting impedance of the skin at the point of contact between the electrodes and the skin. In this embodiment, the treatment applicator is capable of obtaining sensor measurements at high frequencies. In one embodiment, the applicator does not include a sensor and impedance measurements are made at the treatment systems using input signals to the applicators and return signals that change during pre-treatment, treatment, and post-treatment, such as by impedance values increasing, remaining substantially constant and decreasing. For example, in one embodiment, a treatment applicator can record measurements at a sampling rate of about 30 KHz. In various embodiments, the control system includes measurement circuitry operable for measuring impedance values at a sampling rate that ranges from about 20 KHz to about 50 KHz. In one embodiment, the sampling rate ranges from about 1 kHz to about 1 MHz. In some embodiments, the treatment applicator or treatment system is capable of modifying how many times a measurement can be taken such that the sampling rate is user selectable.

Typically, during application of RF energy through one or more electrodes of the array, an increase of impedance was expected. The expected result being informed by a gap or barrier existing once a layer of skin was ablated, charred, and/or vaporized during treatment. This type of gap positioned relative to an electrode results in an increase in impedance. Generally, once cells are removed from a tissue, a vaporization/vapor barrier or air gap appears between the tissue and the electrode tip causing the impedance to increase. This was the expected result.

Unexpectedly, during development, although while the detected impedance increased as treatment is initiated, once the electrodes within the treatment applicator breaks down the outer layer of the tissue, such as skin, the impedance values measured during product development were found to drop. This impedance drop was an unexpected result. Instead of a barrier or air gap being created between the skin and the electrode, the electrode contacts the underlying healthy and hydrated skin that has a lower measured impedance than the layer of skin removed. This unexpected result provides a mechanism for impedance monitoring and customizing treatment based on such monitoring. In various embodiments, treatment is stopped in response to measuring an impedance drop after an initial impedance increase during an RF delivery treatment session.

In various embodiments, the treatment applicator is capable of connecting to a controller and/or analysis system that provides the treatment applicator with RF energy. In at least one embodiment, the controller and/or analysis system can provide between about 150 and about 500 volts RMS (Root mean square power). The controller and/or analysis system are operable to provide the treatment applicator with a configurable amount of RF energy. In various embodiments, the controller system receives sensor data from the treatment applicator to determine when to shut off, or ramp down, the RF energy. In various embodiments, impedance can be used to determine whether a treatment is completed.

Once a treatment applicator breaks through an outer layer of skin using the RF energy, the measured impedance decreases indicating that the treatment applicator is in contact with healthy tissue/untreated tissue. This is preceded by an increase in impedance during a ramp up phase. In some embodiments, the system is operable to measure impedance values at a high rate such as about 30 kHz. In various embodiments, the impedance is measured at the contact point between the pin electrode and tissue under treatment. In various embodiments, impedance measurements are performed in parallel for all of the tissue contacting electrodes in a given array. When applying RF energy to tissue, the impedance level of the tissue increases until the tissue is ablated, charred, and/or removed from the energy source or undergoes another transformation as disclosed herein.

Without being held to a particular theory or mechanism, the impedance level increases due to RF energy heating or drying the tissue. Dehydration of the tissue may be responsible for the initial impedance increase. In this embodiment, once the treatment applicator contacts an untreated layer of tissue, underneath the treated layer of tissue, the impedance level drops in response to the healthy layer of tissue having a greater conductivity relative to the impedance during treatment of the layer transformed by RF delivery. In some instances, the greater conductivity is due to greater hydration of the skin. In at least one embodiment, the controller system shuts off the RF energy when the amount of impedance drops by a certain percentage, threshold, or other value. In various embodiments, the drop threshold is configurable. In some embodiments, the drop threshold (see FIGS. 9 and 10) may be configured based on differences between patients (e.g., amount of skin pigmentation, age, skin hydration, etc.). These impedances changes may be seen in the plots/graphs of FIGS. 6-10.

Figures 2A, 2B, 2C, 2D:
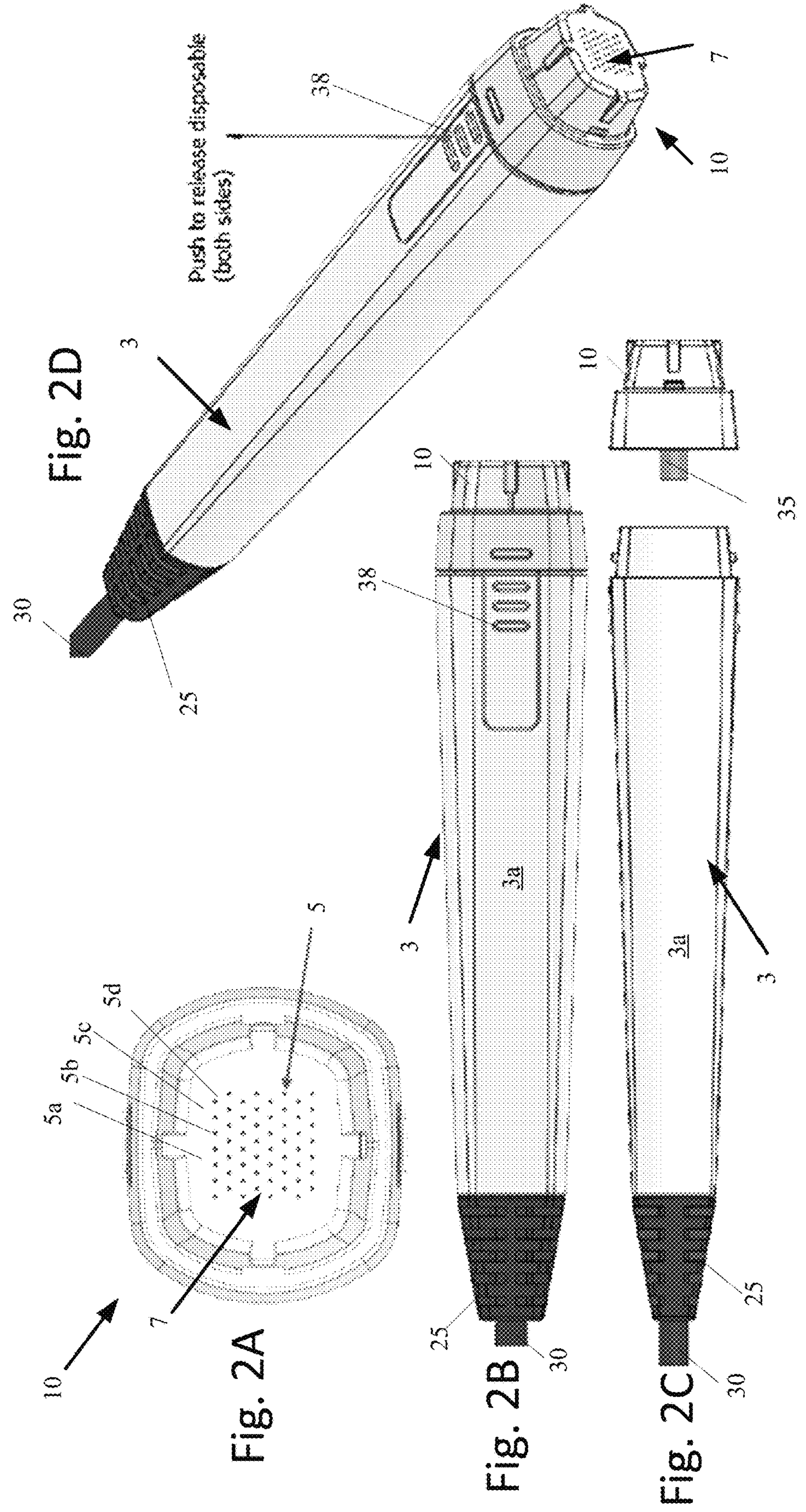
FIGS. 2A-2D are diagrams showing different view of a treatment applicator/probe and components thereof, in accordance with an embodiment of the disclosure.

FIGS. 2A-2D are schematic illustrations of an applicator 5 suitable for directing electromagnetic energy such as radiofrequency RF energy to various tissues of a subject. The applicator may be used in skin rejuvenation treatments, cosmetic treatments, acne treatments, and other treatments as disclosed herein. FIG. 2A shows a view of tissue contacting region of treatment applicator. The applicator may include a plurality of needles (generally shown as 5, but with a row of needles shown specifically as 5_a_, 5_b_, 5_c_, and 5_d_). The needles are arranged according to a pattern with equal of varying spacing therebetween as an electrode array 7. As shown, the needle array 7 is arranged relative to treatment head 10 of the applicator 3. In one embodiment, the needles 5 of the array 7 are each an electrode in one embodiment. In another embodiment, the overall array 7 is an electrode. Each needle includes a tissue-contacting surface.

In various embodiments, one or more RF energy delivery devices transform a region, volume, or portion of tissue. In contrast to other devices, the RF delivery device uses short pulsed RF pulses in conjunction with higher power output. This design facilitates better management of pain during a treatment session, e.g., less pain during treatment. In one embodiment, the period of treatment during which RF energy is delivered ranges from about 3 milliseconds (ms) to about 5 ms. In one embodiment, the RF power delivered ranges from about 200 to about 400 watts. In one embodiment, the RF powered delivered ranges from about 250 watts to about 350 watts. In one embodiment, the range of output voltages delivered to a given tissue region, portion or volume ranges from about 150 volts RMS to about 550 volts RMS.

In one embodiment, the needles are equally spaced and arranged relative to the vertices of hexagon with one needle disposed at the center of the hexagon to define an equal spacing of about 60 degrees relative to a given central needle. In one embodiment, the distance between needles ranges from about 0.5 mm to about 3 mm. In one embodiment, the needle spacing is about 1.5 mm. The treatment array may range from about 1 mm×about 1 mm to about 30 mm×30 mm. For various embodiments, each of the electrode (needle/pin) in a given electrode array are connected in parallel and monitored in parallel such as during impedance, voltage, resistance, current, and other input, output, and treatment session specific measurements. In some embodiments, a hybrid or selectively addressable electrode array is used with one or more control circuits operable to activate a subsets of electrodes in a larger array designed to cover a larger treatment area.

As shown, the treatment applicator head 10 includes an interior portion having an array of holes through which electrode pins can be extended and/or retracted. In some embodiments, electrodes are fixed in an extended position. FIG. 2B shows a side view of a treatment applicator 3 having a tapered shaft, with a first end including a treatment applicator head 10 and a second end or applicator terminus 25 in communication with an analysis and/or control system. One or more cables 30, such as nested cable within a common jacket extend from the terminus and connect to the analysis and/or control system. The one or more cables may include electrical cables for power and control signal delivery. In turn, the treatment head 10 may include one or more ports or surfaces in fluid communication with a coolant reservoir or other coolant system. In addition, the treatment head may include suction ports in fluid communication with conduit that is bundled with and/or one of the one or more cables/conduits 30. The treatment head 10 may be attached to body 3_a_ of applicator 3 through various fasteners/attachment assemblies 35.

As shown in FIG. 2C, the treatment applicator head is removably attached to the treatment applicator. Upon activation of a switch 38, the treatment applicator is capable of separating from the body 3_a_ of the treatment applicator 3. In some embodiments, the switch is slidable. In other embodiments, the switch is depressible. Various compression fit and other tension based attachment mechanisms may be used to releasably couple the treatment head 10 to body 3_a_. In various embodiments, the treatment applicator is disposable after use. In certain embodiments, the treatment applicator head 10 is removable for cleaning and/or sterilization.

Figure 3A:
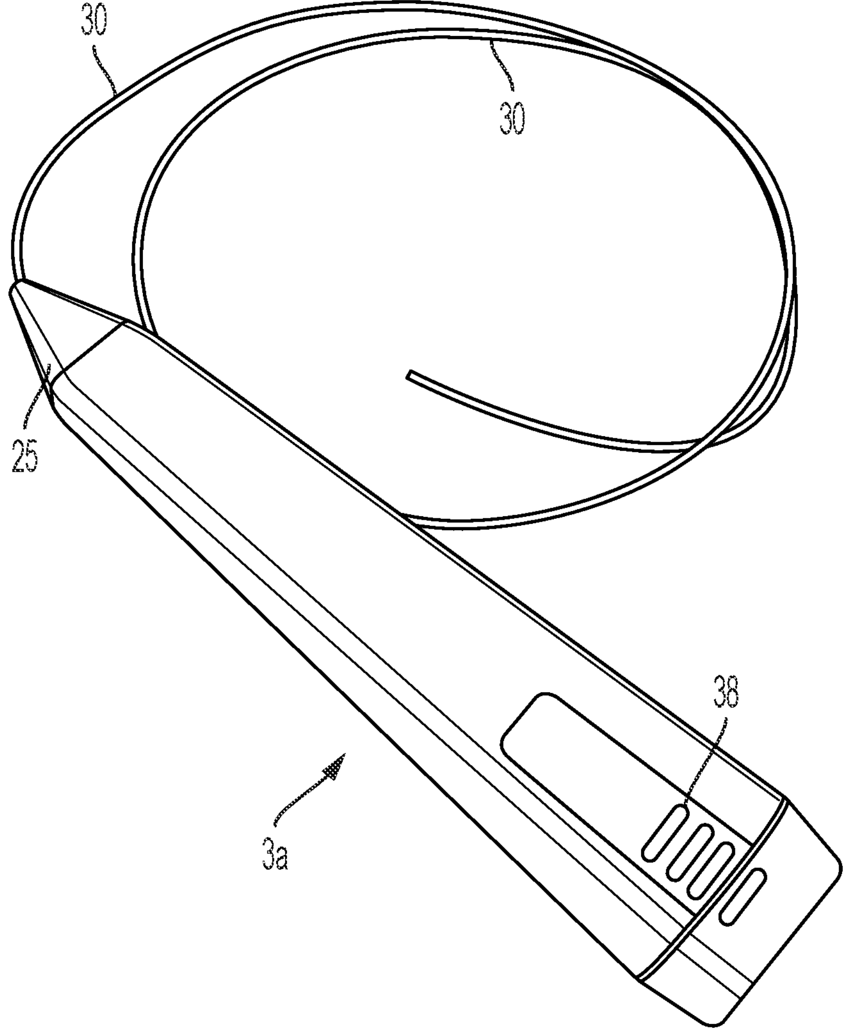
FIG. 3A is an alternate perspective view of a body of a treatment applicator suitable for tissue treatment, in accordance with an embodiment of the disclosure.

FIG. 3A is a perspective view of a treatment applicator body 3_a_ depicted in FIGS. 2A-2D and suitable for use in skin rejuvenation and for other treatments, in accordance with an embodiment of the disclosure. As shown, the body of the treatment applicator is without the removable treatment applicator. The body of the treatment applicator includes a second end or terminus 25 connected to a communication cable 30 capable of coupling to an analysis and/or control system.

Figure 3B:
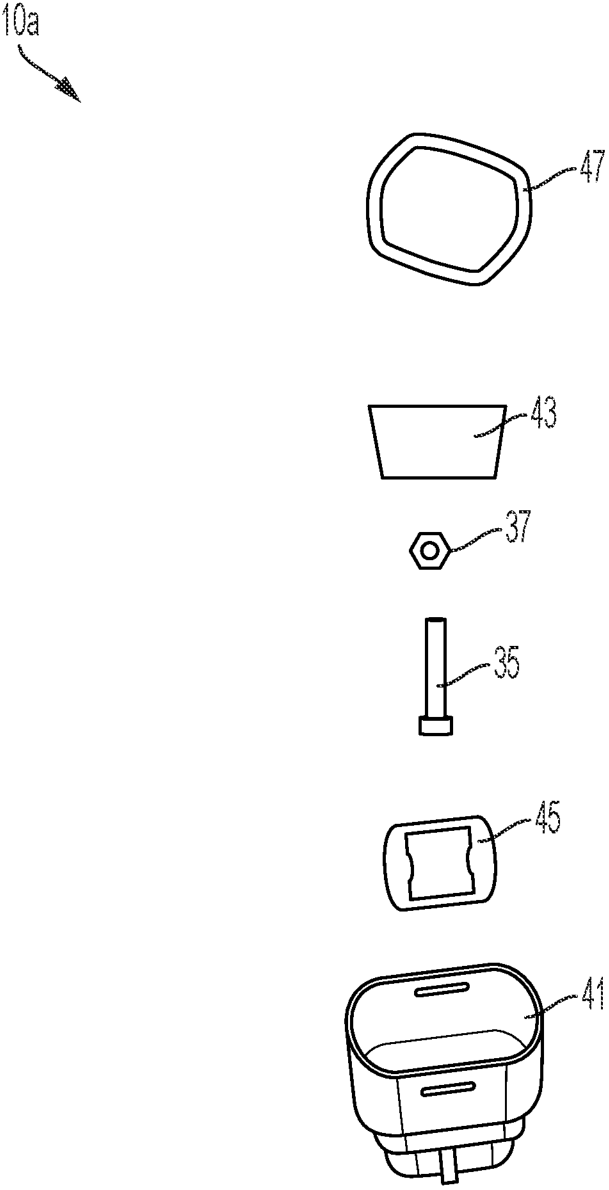
FIG. 3B is an image showing an exploded view of some exemplary components of a treatment applicator head, in accordance with an embodiment of the disclosure.

FIG. 3B is an exploded view of a treatment applicator head 10_a_, in accordance with an embodiment of the disclosure. The applicator head can be used in conjunction with applicator body 3_a_, such as for example shown in FIG. 3A, and an electrode array and other components to form an overall treatment applicator. The treatment applicator head 10_a_ shown includes a fastening element 35, a securing element 37 such as a nut (as shown) an outer housing 41, an inner housing 43, a first support or gasket 45, and second support or gasket 47. A given support or gasket may fit within or otherwise be disposed or arranged relative to a given housing. References to first and second supports is non-limiting and either support may be initially referred to as first with a subsequent support being identified as a second support without limitation. An electrode array or assembly such as a conductive plate with conductive pins or needles in electrical communication therewith is also incorporated into the treatment head such that the pins or needles extend outward in tissue facing direction. The head 10_a_ may also include one or more conduits and ports defined by one or more of its surfaces suitable for suctioning air, smoke, fluids, etc., and/or delivering coolant, medicament, or other liquids or gels to a reservoir in the head or to the tissue.

Figure 4:
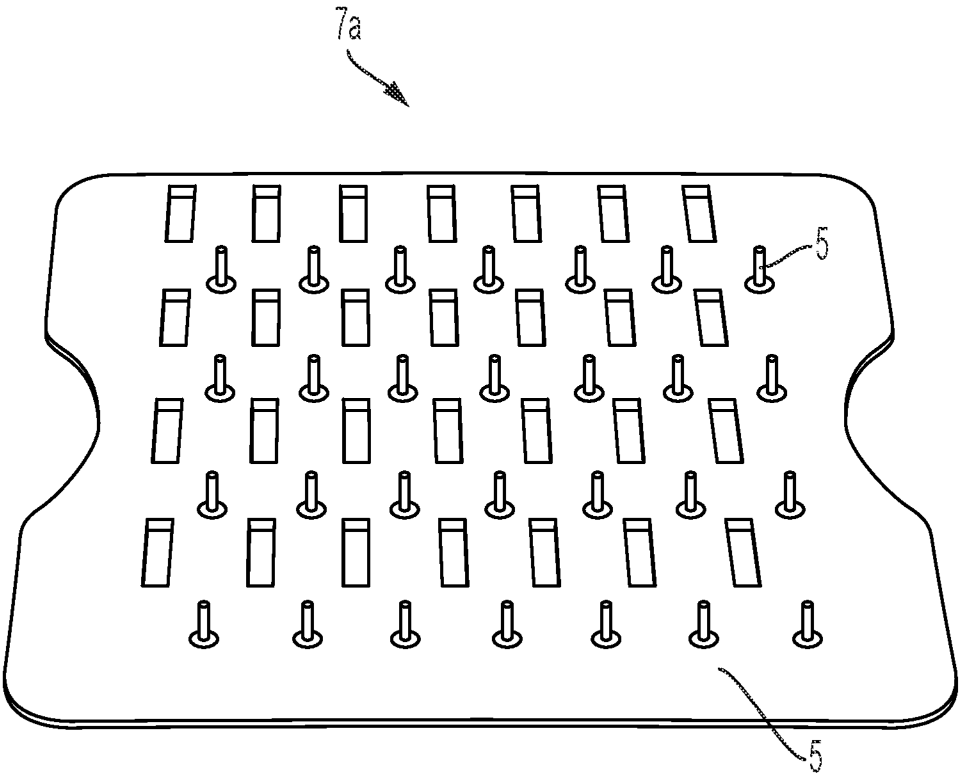
FIG. 4 is a diagram of metal conductive pin/needle electrodes for use in a treatment applicator, in accordance with an embodiment of the disclosure.

FIG. 4 is an n electrode array 7_a_ that includes a plurality of needles 5 for use in a treatment applicator, in accordance with an embodiment of the disclosure. As shown, the electrodes are coupled to a single pad aligned in rows. When installed within a treatment applicator, individual electrodes within the electrode may be individually controllable. In one embodiment, the pins or needles (e.g., non-penetrating needles or blunt needles) and the plate they extend from is a unitary conductive structure. The electrode array comprises a metal, or one or more metals, such as an alloy. In one embodiment, all of the electrodes are addressed and measured in parallel using a control system.

Figures 5A, 5B, 5C:
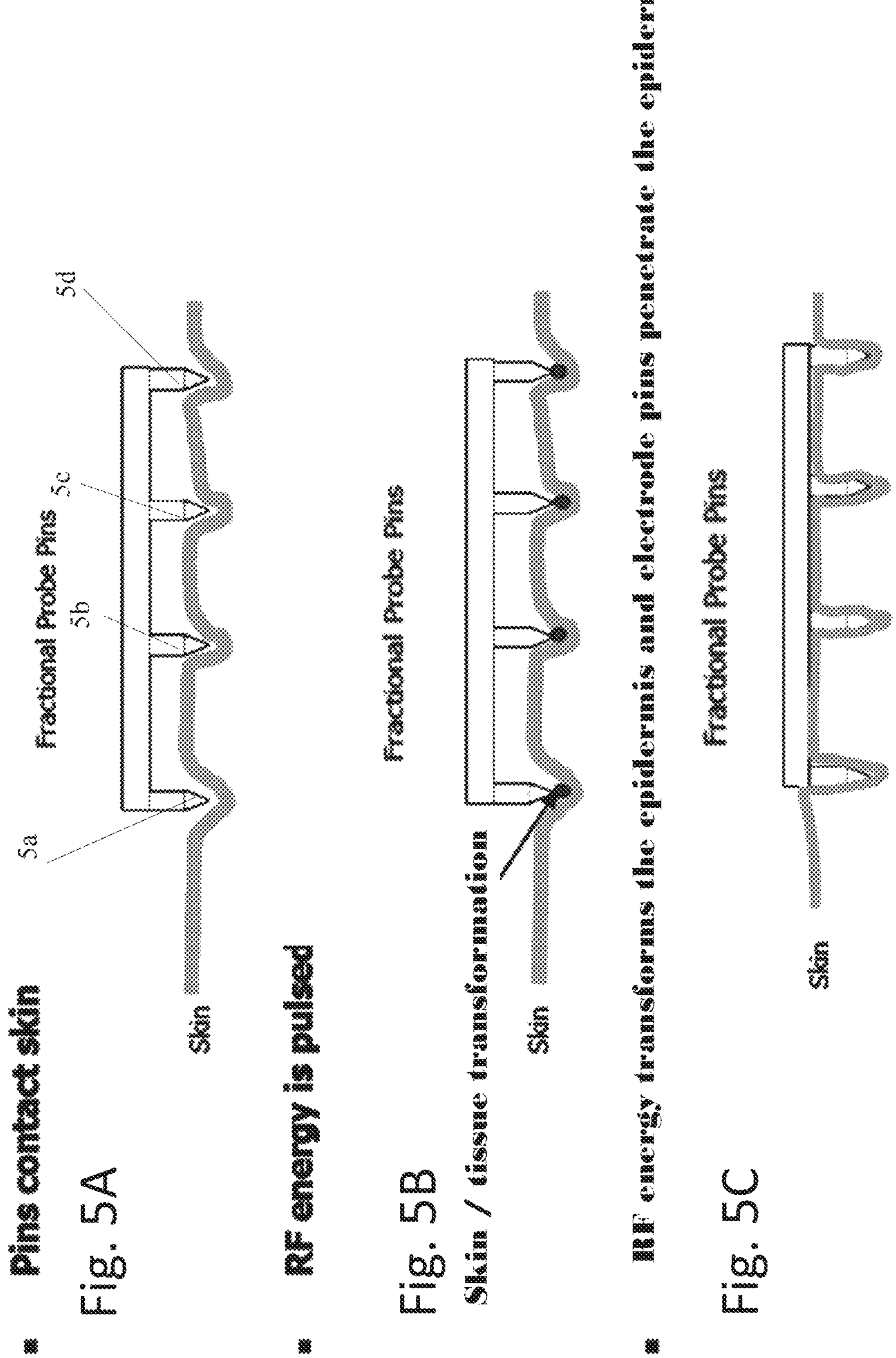
FIGS. 5A-5C are simplified illustrations of an array of electrodes from a treatment applicator applying RF energy to skin, in accordance with an embodiment of the disclosure.

FIGS. 5A-5C are simplified cross-sectional illustrations of an array of electrodes from a treatment applicator applying RF energy to skin, in accordance with an embodiment of the disclosure. A row of electrodes in the array includes needles or pins 5_a_, 5_b_, 5_c_, and 5_d_ as depicted. In one embodiment, the pins or needles 5 are also referred to as fractional probe pins/needles. The pins/needles 5_a_-5_d_ represent a subset of the electrodes from a treatment applicator (as shown in FIGS. 2A-2D or in FIG. 1C). As shown, the needles and the overall electrode array are being placed in contact with a treatment region of tissue, in this case skin. In one embodiment, the deformation of the skin at the needle contact points is achieved by the operator pressing the surface of the electrode array into the skin. In other embodiments, the pins/needles of the array rest on the surface of the skin and descend into the skin as the tissue subsequently is transformed or removed after the application of RF energy through one or more of the pins or needles or all of such pins or needles.

Once in contact, a controller and/or analysis system pulses RF energy through each of the electrodes. The pulsed RF energy causes a transformation of the tissue such as a removal of tissue at the point of contact or other transformations or transforming processes as disclosed herein. In some embodiments, the skin tissue transformation (shown in FIG. 5B) causes the removal of tissue. In other embodiments, the electrodes become heated causing the tissue in contact with each electrode to become charred and removed from the skin. In some embodiments, the tissue in contact with the electrodes evaporates from the use of the RF energy. In other embodiments, one or more transformations including combinations of different transformations occurs as disclosed herein with regard to the tissue after RF energy is applied to the electrode array.

In various embodiments, the tissue undergoes a transformation such that tissue is removed and the pins/needles of electrode array move into volumes of tissue previously occupied by tissue that has been transformed and effectively removed from the subject or changed in form such as through compaction, vaporization, charring, plasma formation, or another transformation initiated or caused by RF energy delivery. As tissue is removed (as shown in FIG. 5C) the electrodes come in contact with underlying healthy tissue. A given tissue may have one or more parameters that vary with a given subject such as pigmentation, hydration, tissue thickness, etc. In some embodiments, tissue may smoke or be vaporized which can be removed through a fluid transfer device which may be part of or a separate device from the applicator.

In various embodiments, upon placing a treatment applicator on skin and transmitting RF signals/energy to the skin, the control system or an impedance detection subsystem in communication with the treatment applicator measures impedance values of the skin. As RF energy is applied to the skin through each of the electrodes, the impedance measured increases due to the tissue transformations occurring where the electrode array contacts a region of tissue. As the RF energy causes one or more tissue transformations such as lesions, the impedance of the tissue slowly increases as the tissue is removed or otherwise transformed.

Once the electrode array has penetrated further into the tissue and in contact with the underlying tissue layers, a drop in impedance is detected. In one embodiment, the drop or decrease in impedance is correlated with the electrode array contacting a more conductive tissue layer below the tissue which was recently undergoing transformative treatment. The initial increase in impedance is referred to as a ramp up in impedance and the subsequent unexpected decrease in impedance is referred to as a ramp down in impedance. Aspects of the applicator and/or array(s) disclosed in connection with FIGS. 2A-5C, and various other figures, maybe used in connection with other array(s) and/or applicator(s) disclosed herein e.g., in FIGS. 1B, 1C, 2A, etc.

Figure 6:
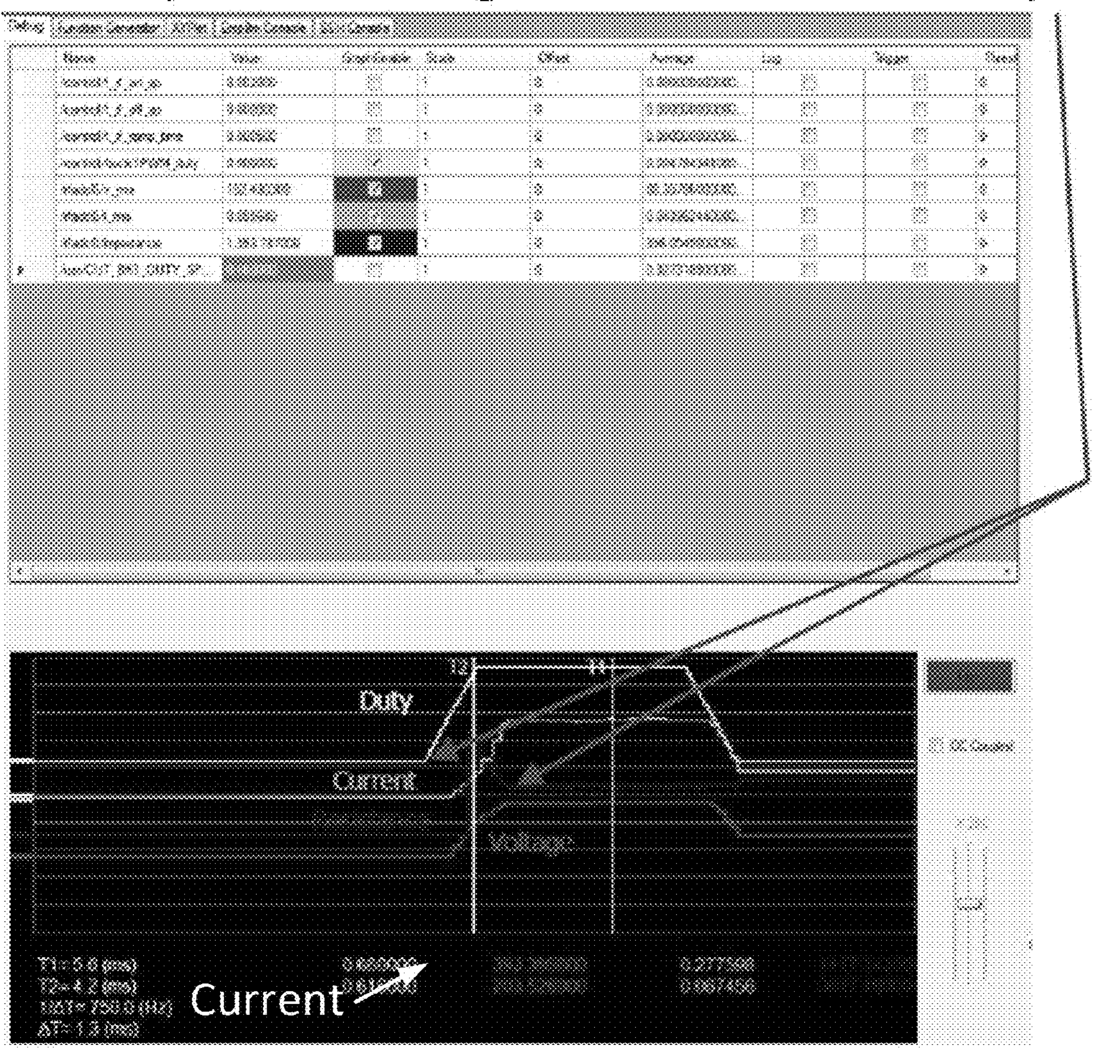
FIG. 6 is a display showing electrical signals during pre, post, and during a tissue treatment using a treatment applicator, in accordance with an embodiment of the disclosure.
Figure 8:
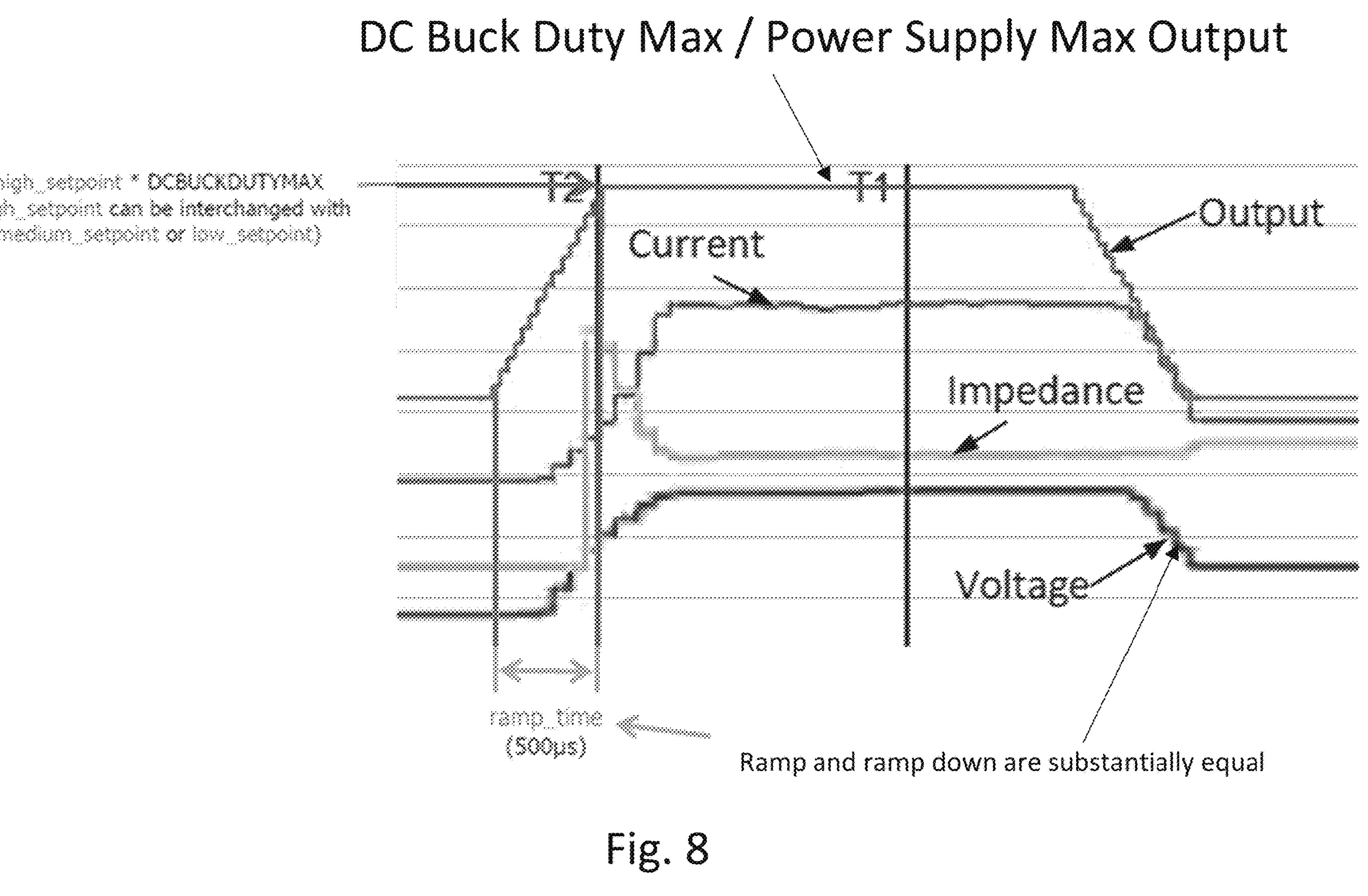

FIG. 6 is a display showing the effect of treating a portion of skin, in accordance with an embodiment of the present disclosure. As shown, the graph displays duty (i.e., power output from the system), current delivered by the treatment applicator, detected resistance and measured voltage. As shown, duty corresponds to the duty cycle of the DC buck converter transistors, which corresponds to the output DC voltage from the DC buck converter. 0 duty is 0 voltage, while a duty of 1.0 is max DC voltage in various embodiments. In various embodiments, the system controls RF output voltage (applied voltage to the subject) because, into a given load impedance, the buck DC voltage is proportional to the RF output voltage. In various embodiments, the power supply maybe have a range of voltage outputs including various setpoints such as a high, medium and low setpoint as shown in FIG. 8. The DC buck duty max as referenced herein refers to the maximum output voltage of the power supply. In one embodiment, the power supply is a buck boost power supply. The resistance shown in various figures and otherwise discussed herein is correlated with or the same as impedance in various embodiments.

Prior to the delivery of the RF energy, the measured resistance is about 3017 ohms with an associated current of about 67 mArms and a voltage of about 204 Vrms. The resistance curve, which is plotted based on measured or calculated resistance values, initially ramps up and then ramps down. After the treatment energy has been delivered to the tissue of interest, the resistance ramps down to about 1417 ohms with an associated current of about 277 mArms and a voltage of about 393 Vrms. This change in resistance/impedance occurs about 600 μseconds after the start of the resistance/impedances ramping up in one embodiment. In various embodiments, a period of tissue treatment occurs after the detection/measurement of the decrease in resistance/impedance after its initial increase/ramp up.

Figure 7:
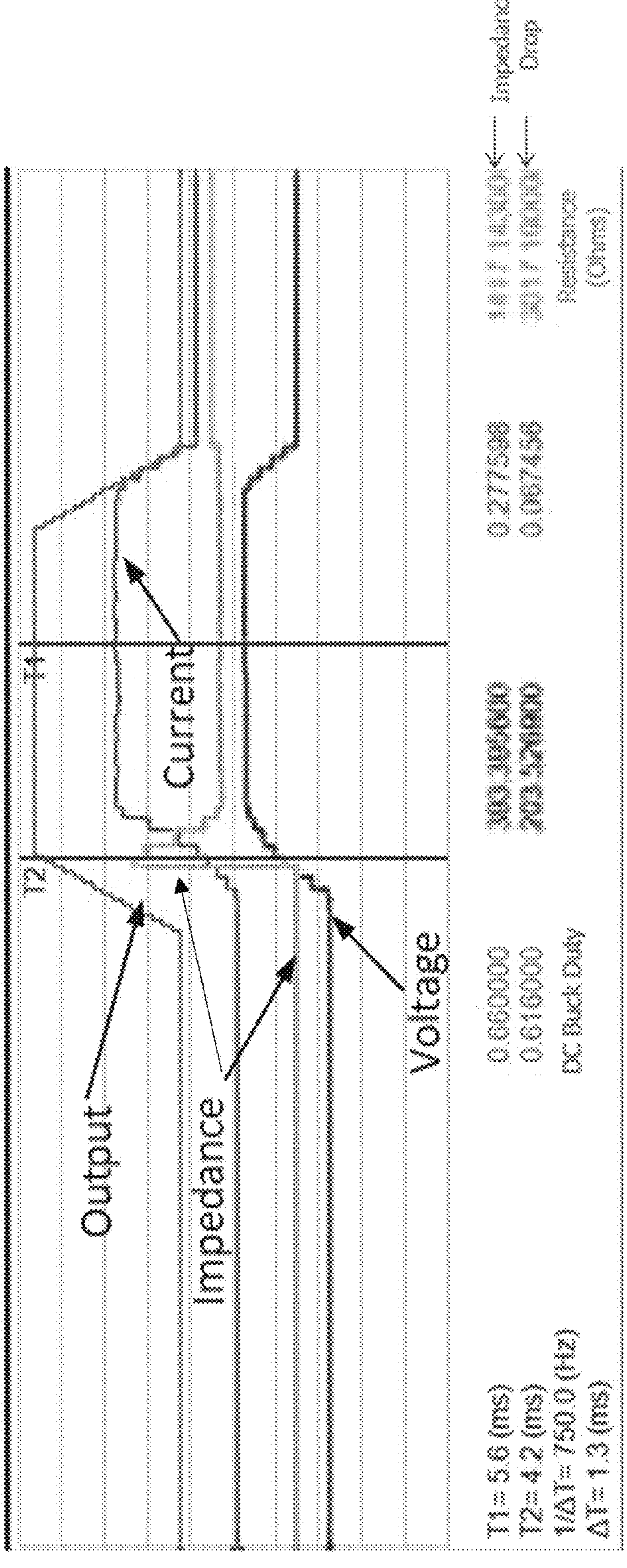
FIGS. 7-10 are graphical displays depicting electrical signals including current, impedance, and voltage during various time periods including during tissue treatment with RF energy applied using a treatment applicator, in accordance with an embodiment of the disclosure.

FIG. 7-10 are graphical displays showing different electrical signals and changes thereto during application of RF pulse energy from an electrode array of a treatment applicator, in accordance with an embodiment of the disclosure. As shown in FIG. 7, the display graphs power output, current, impedance, and voltage with respect to time. Upon start of a treatment, the output power is ramped up for approximately about 500 microseconds. Optionally, in another embodiment, the upon start of a treatment, the output power is ramped up for from about 100 microseconds to about 5 ms, or from about 500 microseconds to about 1 ms. As shown, line T2 indicates the time in which a max impedance is reached. T2 also corresponds to occurrence of a max resistance in various embodiments. T2 also shows the start of a substantially flat output power after a ramp up before T2. T1 indicates a time after the impedance has dropped and reached a flattened steady state. The entire pulse happens within a few milliseconds, where the difference between T1 and T2 is about 1.3 ms.

Figure 9:
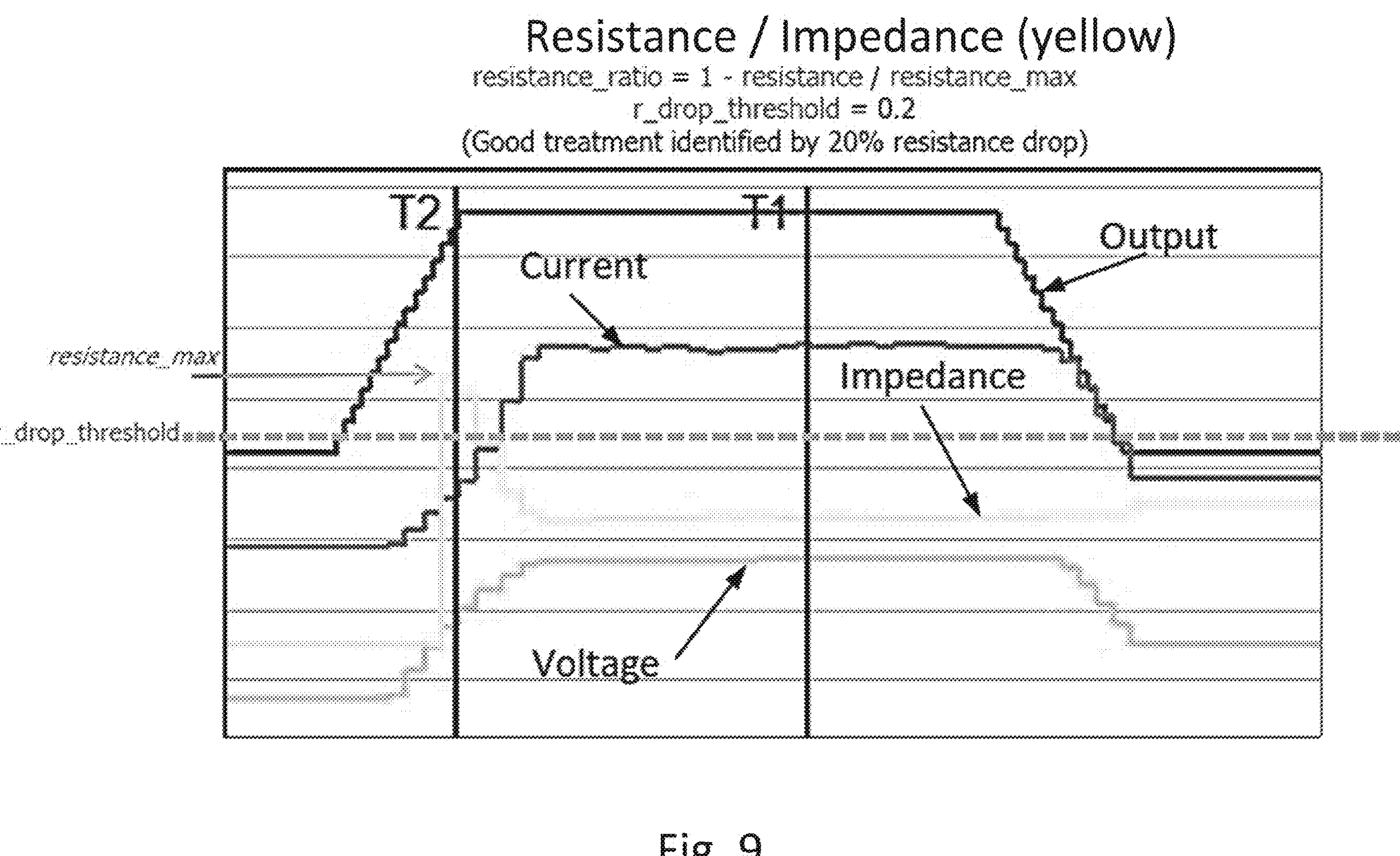

In one embodiment, the time of RF energy delivery ranges from about 0.3 ms to about 50 ms. In one embodiment, an impedance drop value, also referred to herein as impedance or resistance threshold or threshold drop. In FIG. 9, it is identified as r_drop_threshold. The threshold drop corresponds to a threshold for determining that impedance drop has been achieved. Once the resistance/impedance drop has occurred that meets or exceeds the expected threshold drop, the control system initiates a timer for the treatment with RF energy to continue. In various embodiments, different impedance/resistance threshold values can be specified for different tissues/parts of the body. The time period from T2 to the ramp down of the output voltage correspondence to the treatment time in some embodiments.

At time T1, electrodes from the treatment applicator have broken through an outer layer of tissue and are in contact with the underlying tissue. The conductivity of the underlying tissue is greater than the tissue being treated in one embodiment. In various embodiments, the treatment time is the substantially flat region of the plot of output power between the upward slowing ramp up line and the downward sloping ramp down line, the plateau region between the ramps. In one embodiment, the ramp time is managed to reduce or prevent muscle tissue from twitching or otherwise experiencing involuntary contraction/spasms. In one embodiment, the ramp time ranges from greater than about 0 to about 500 ms. In another embodiment, the output voltage ramp time is approximately or about 500 microseconds. Optionally, in another embodiment, the output voltage ramp time ranges from about 100 microseconds to about 5 ms, or from about 500 microseconds to about 1 ms. In one embodiment, pulse duration and output power are selectable by a user and can be adjusted based on one or more parameters associated with a given treatment subject/tissue type.

In various embodiments, when operating a treatment system, a user is able to select an operation setpoint and pulse duration. In various embodiments, a set point indicates the amount of RF energy sent through the treatment applicator. A setpoint variable may be set to high, medium or low. These can be set automatically using measured impedances or can be user specified based on an operator's experience with various tissue types/skin parameters. In various embodiments, a pulse duration corresponds to an amount of time the RF energy pulse is active. In at least one embodiment, the pulse duration can be set between about 1 ms and about 12 ms.

In various embodiments, pulse duration can be modified based on a prescribed treatment. In some embodiments, a foot pedal is incorporated to control initiation of a pulse within the system. In these embodiments, an RF pulse initiates upon depression of the foot pedal and terminates whether or not the user releases the pedal. In one embodiment, maximum operation frequency is about 1.5 Hz. In another embodiment, maximum operation frequency is about 3 Hz. In still another embodiment, the maximum operation frequency is about 5 Hz. The operation frequency can range from about 0.5 Hz to about 10 Hz, from about 0.5 Hz to about 5 Hz, or from about 1.5 Hz to about 5 Hz. In various embodiments, operation of the system produces an audible tone lasting about 500 ms. In various embodiments, the treatment applicator is implemented with a maximum power output of about 200 watts. Each of the set points corresponds to an amount of RF output provided by the system. Some examples of various system values and are outlined in the table below and related scaling factors discussed below the table.

| Variable | Default value | unit |
|---|---|---|
| high_setpoint | 1.2 | N/A |
| med_setpoint | 1.0 | N/A |
| low_setpoint | 0.8 | N/A |
| r_drop_threshold | 0.2 | N/A |
| t_resistance_drop_sp | 0.003 | s |
| ramp_time | 0.0005 | s |

Each of the foregoing values are "about" the value shown and may vary over a ranges such that each value in table spans a ranged bounded by a given value being multiplied or divided by a factor selected from the group ranging from about 1 to about 50.

For example, in one embodiment, "high" corresponds to ramp up DC buck duty to high_setpoint*DCBUCKDUTYMAX. "Medium" corresponds to Ramp up DC buck duty to_med_setpoint*DCBUCKDUTYMAX. "Low" corresponds to Ramp up DC buck duty to_low_setpoint*DCBUCKDUTYMAX. In various embodiments, DC BUCKDUTYMAX refers to a maximum amount of RF energy able to be provided by a controller and/or analysis system in communication with a treatment applicator.

As shown in FIG. 8, the set point is set to "high" and has a ramp up and ramp down time of 500 μs. In this example, the ramp up and ramp down time is set to minimize the possibility of a muscle reaction when applying RF energy to the skin.

As shown in FIG. 9, the controller and analysis system is configured with a drop threshold of 0.2, which is equivalent to a 20% drop in impedance. In this instance, the treatment is successful, which is shown by the 20% resistance drop between T2 and T1. The r_drop_threshold value is shown by the dotted line and shows an initial rise in impedance and then a decrease in impedance after T2. In one embodiment, treatment period starts at T2 and continues for a period of milliseconds as disclosed herein. In various embodiments, the impedance/resistance drop threshold ranges from about 5% to about 80%, or from about 10% to about 90%, or from about 20% to about 50%.

Figure 10:
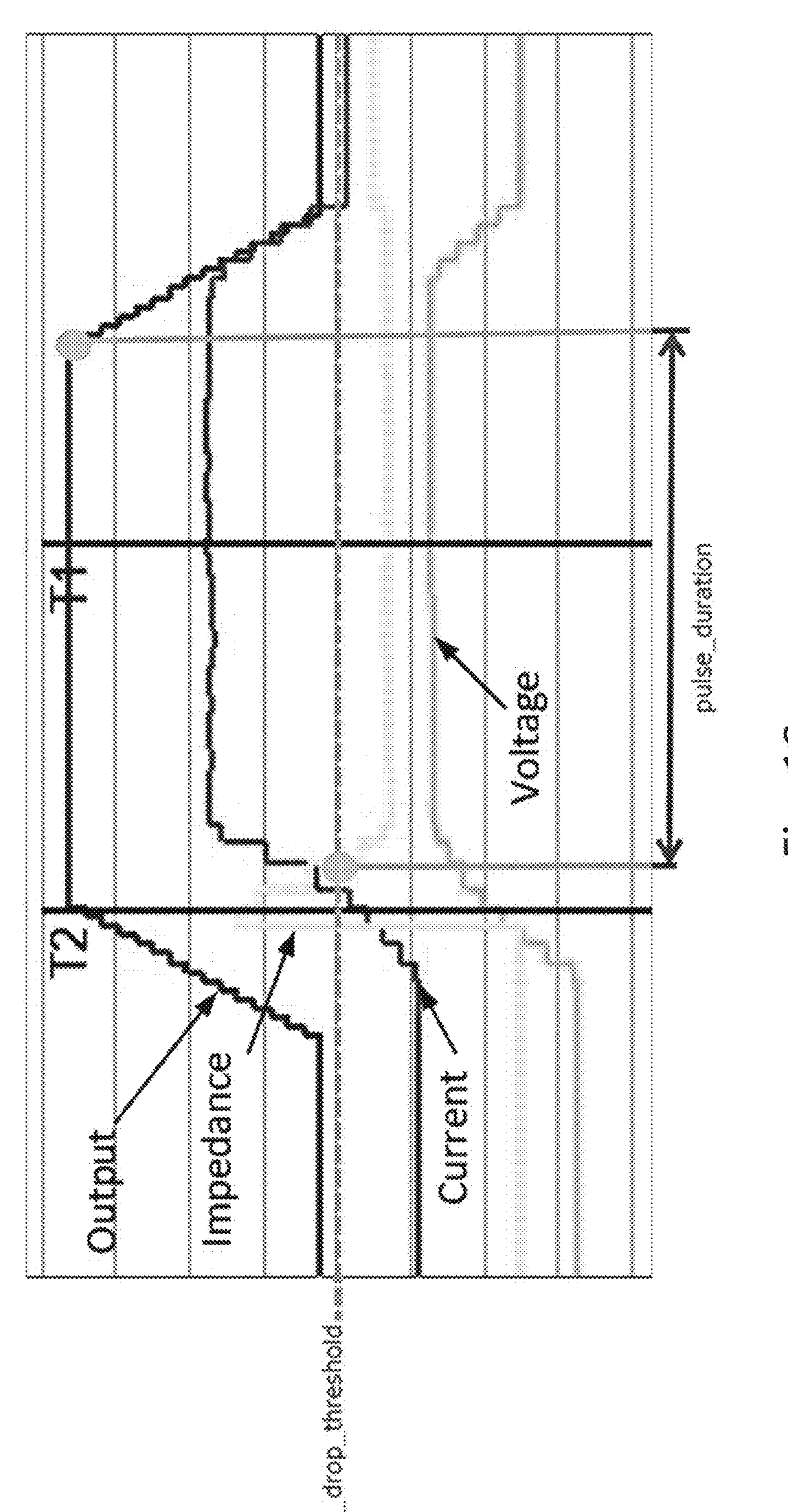

As shown in FIG. 10, a treatment time is defined by the drop threshold and the pulse duration. Treatment time starts when the impedance has dropped by an amount equal to the drop threshold, shown as r_drop_threshold having the dotted line as shown. The pulse duration is set by user in various embodiments.

Figure 11A:
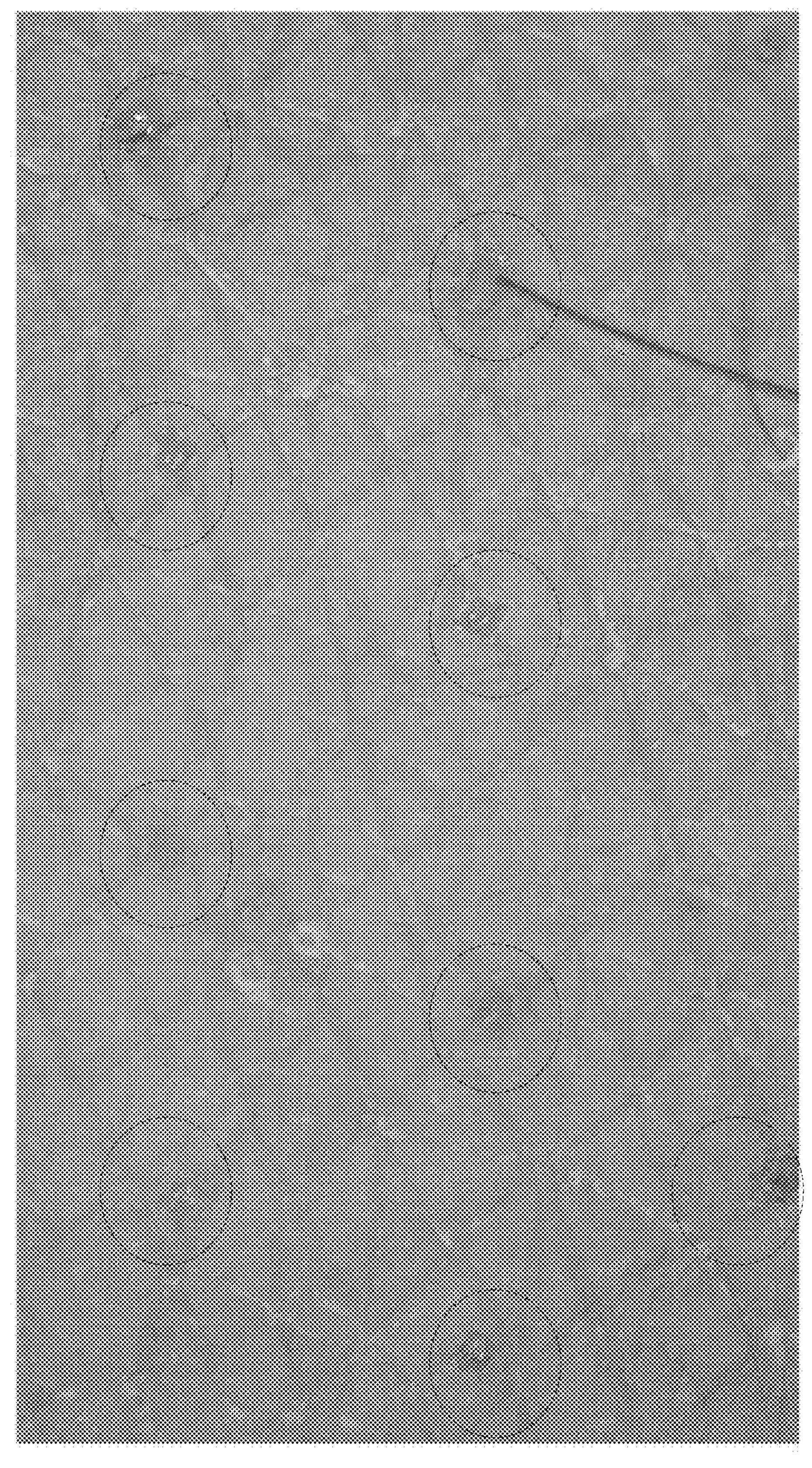
FIG. 11A is a first photographic image of tissue after being treated using a treatment applicator for a treatment duration determined using impedance monitoring, in accordance with an embodiment of the disclosure.

FIG. 11A is a photograph of skin after being treated, in accordance with an embodiment of the present disclosure. As shown, a treatment applicator has created a fractional treatment pattern within the skin and an outer portion of tissue has been removed. The regions of contact with electrodes are shown by dotted circles. The treatment duration used was selected in response to impedance monitoring and is tailored to the individual being treated. In this way, a given subject's hydration level, age, pigmentation, tissue condition and other factors can be factored into setting the treatment duration by performing impedance monitoring. Referring also to FIG. 1B, the tissue injury depicted, including the well/crater W shown in FIG. 1B, is a rendering of the cross section of one of the circled injuries of the fractional treatment pattern shown in FIG. 11A.

The pattern of fractional injury shown has some advantages when performing skin rejuvenation. With a fractional treatment pattern, the injured portions of the epidermis are islands of injury surrounded by healthy/untreated tissue. The surrounding healthy/untreated tissue allows the treated tissue to heal/recover faster. This faster healing from smaller distributed fractional injuries is in contrast with an approach where a larger aggregate treatment injury to all of the tissue in one area, which has a slower overall all recovery time period. A fractional approach can facilitate faster tissue repair and rejuvenation compared to a larger aggregate treatment approach.

Figure 11B:
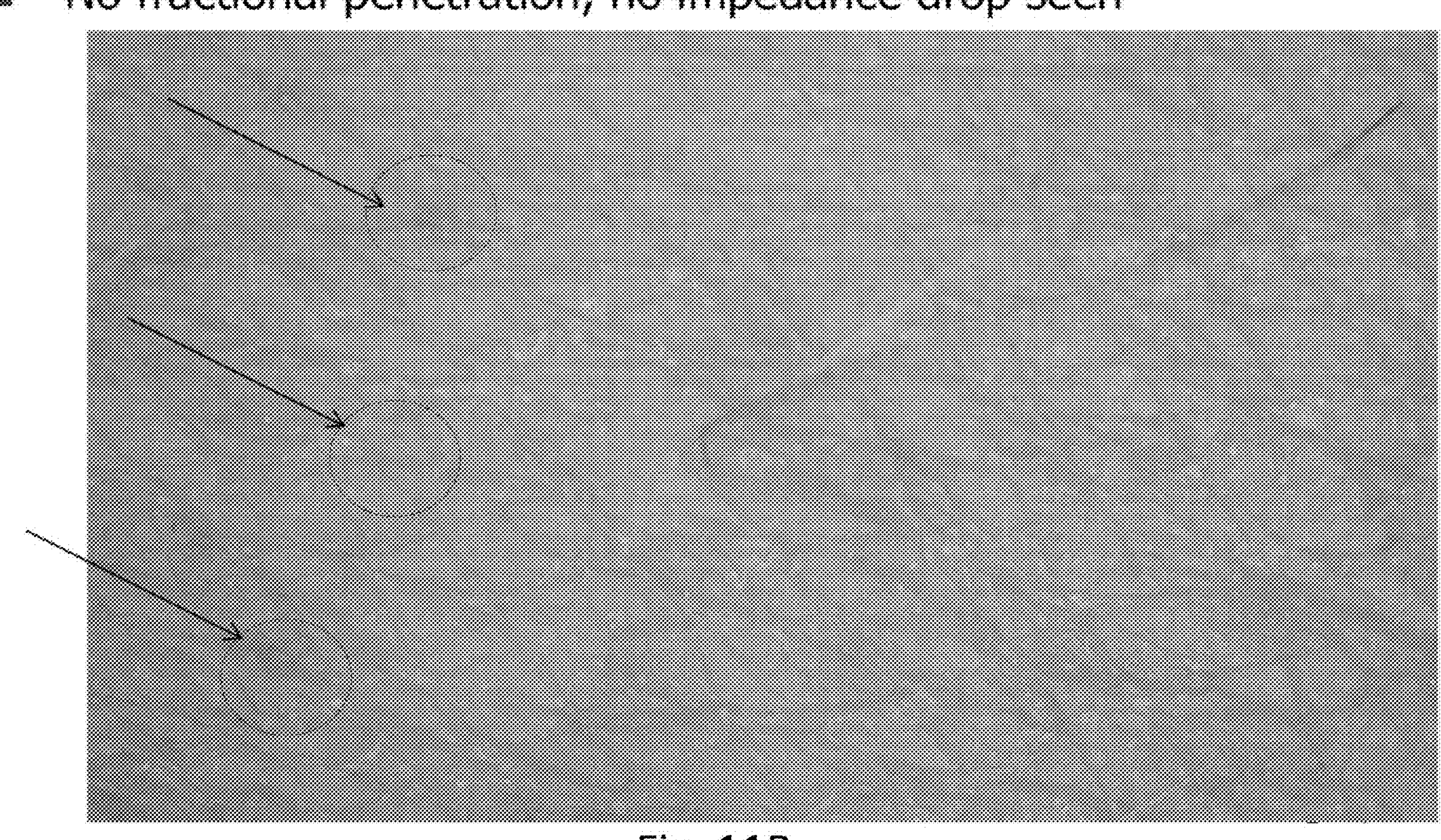
FIG. 11B is a second photographic image of tissue after being treated using a treatment applicator for a period of time less than the recommended treatment duration, in accordance with an embodiment of the disclosure.

FIG. 11B is a photograph of skin that has been treated, in accordance with an embodiment of the disclosure. In contrast to FIG. 11A, FIG. 11B shows that the treatment was not successful. In this case, the duration of the treatment did not continue long enough to remove the outer layer of tissue. Regions where treatment was attempted are shown by dotted circles. As such, the treatment did not remove enough tissue to reach the underlying healthy tissue.

The observed fractionated superficial skin injury after RF Fractional treatment with an example device as described above is shown on FIG. 1A. A histological clinical study was performed to evaluate the observed superficial skin injury on a microscopic scale.

A patient scheduled for abdominoplasty was recruited for the histological clinical study. Prior to abdominoplasty, the area scheduled for excision was marked and divided into four treatment regions (1, 2, 3, and 4). In regions 1 and 2, treatments with impedance sensing guided timing were evaluated with and without skin moisturizing prior to treatment. In regions 3 and 4, treatments without impedance sensing guided timing, or normal timing, were evaluated with and without skin moisturizing prior to treatment. Skin moisturizer was applied in regions 1 and 3 half hour prior to treatment. In all four regions treatment power level was varied between levels 1, 2 and 3 and power delivery duration ranges from between about 1 ms and about 8 ms. The applied moisturizer was provided to regions 1 and 3 to improve consistency of the electrical properties when RF Fractional was applied to the treatment area.

Figure 12A:
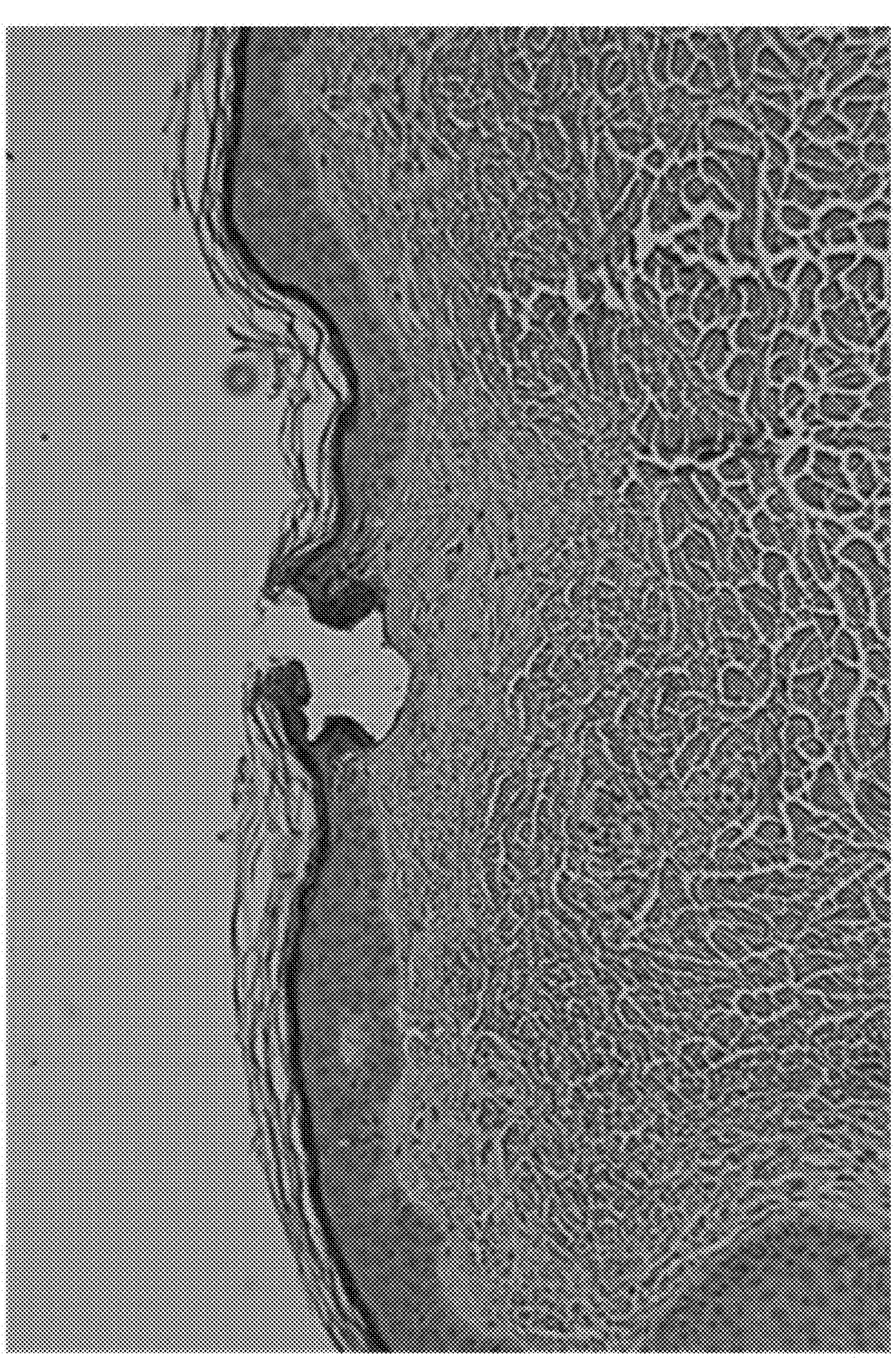
FIG. 12A is a histology image of tissue obtained from a first region with applied moisturizer prior to treatment with an RF on-time of about 3 ms in accordance with an embodiment of the disclosure.
Figure 12B:
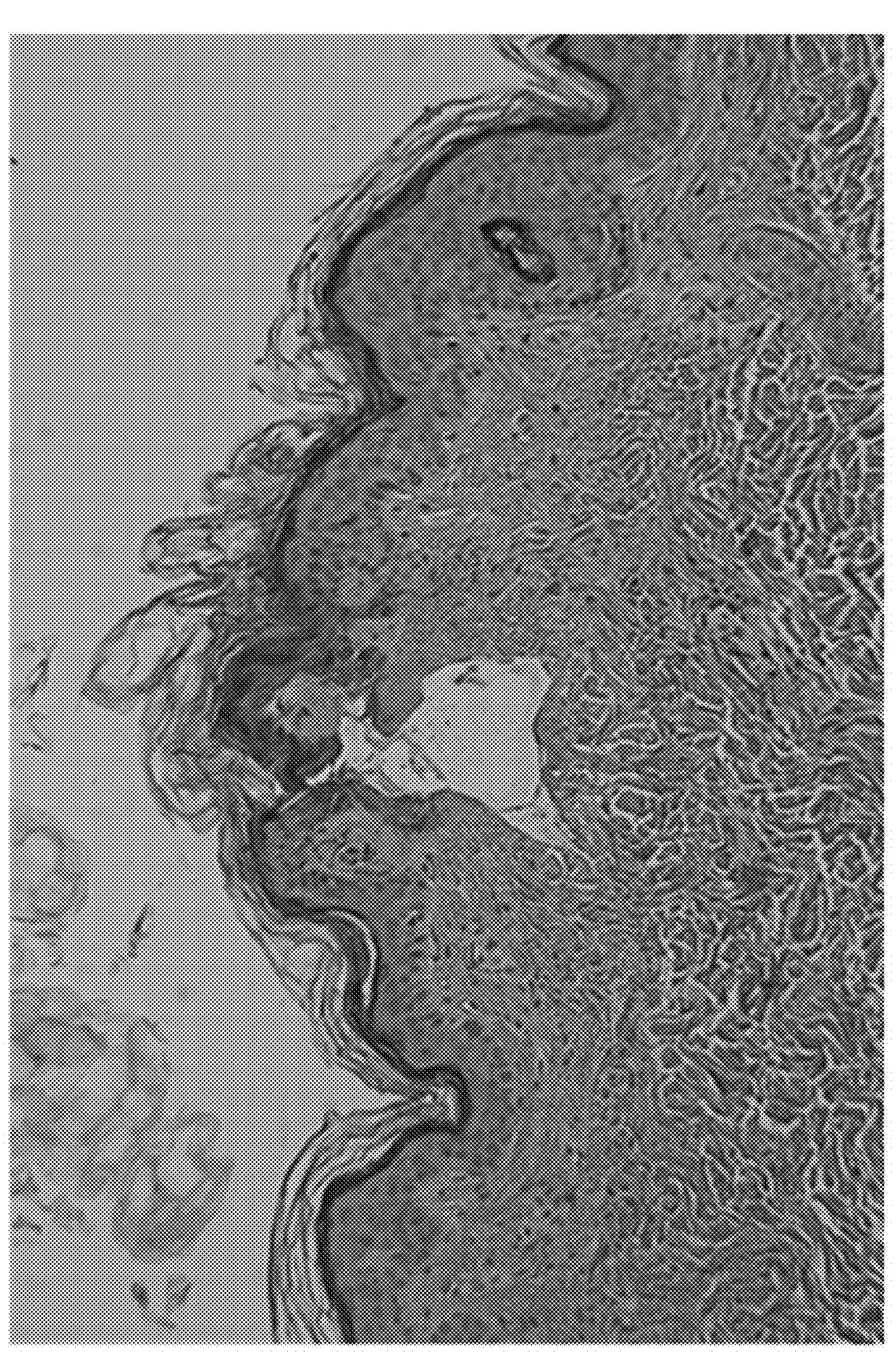
FIG. 12B is a histology image of tissue obtained from a first region with applied moisturizer prior to treatment with an RF on-time of about 5 ms in accordance with an embodiment of the disclosure.

All treatments were performed while the patient was under anesthesia. After excision of the abdominoplasty surgery area, approximately 6 mm punch biopsies were obtained from each treatment region. The biopsies were processed with hematoxylin/eosin (H&E) staining and evaluated under an optical microscope. Example microscopy photos are shown on FIGS. 12A and 12B. Both photos show histology taken from region 1 with applied moisturizer prior to treatment at level 3 with impedance sensing guided timing. The tissue in FIG. 12A was treated with about 3 ms on-time, tissue in FIG. 12 B was treated with about 5 ms on-time.

The histology observations made by a practicing dermatologist whose practice includes reading dermatological histology were: "Complete fractional epidermal and superficial papillary dermis ablation with wounding restricted to the adjacent 60 to 80 micrometers of papillary dermis. Ablation depth increases with extending the on-time. Topically applied moisturizer results in greater consistency in the histological findings versus the samples where there was no topically applied moisturizer."

The observed ablated region and the wounding of the papillary dermis serves as a conduit for a topically applied compound or mixture of compounds. Large molecules as well as non-lipid soluble topicals or other topicals not well absorbed through intact epidermis may be selected to have greater absorption with the fractional skin features created using the systems, devices, and methods disclosed herein. Examples of topical materials and molecules/compounds that would be expected to have greater absorption with the fractional skin features: growth factors; antioxidants such as vitamin C or other molecules with similar properties; PRP (platelet rich plasma); Tranexamic acid; Azelaic acid. Various aqueous and non-aqueous lotions and topicals may be used in various embodiments. Conditions addressed by such topicals having enhanced penetration can include acne, melasma, acne scars, scars, wrinkles, uneven pigmentation, redness, and rosacea.

The histological injury involving the epidermis and the dermis created using the systems, devices, and methods disclosed herein are often similar to those created by low power fractional $CO_2$ and fractional Er:YAG treatments. Therefore, the data collected on drug penetration with fractional $CO_2$ and fractional Er:YAG devices would be applicable to the RF fractional injuries created by this device. Drugs that have been studied for drug penetration with fractional $CO_2$ and fractional Er:YAG and similar drugs may be used for RF fractional injuries assisted delivery. Examples of drugs and substances reported to have enhanced skin penetration with fractional $CO_2$ and fractional Er:YAG devices are provided in Hcedersdal, Merete, et al. "*Fractional $CO_2$ laser-assisted drug delivery.*" *Lasers in Surgery and Medicine:* 42.2 (2010): 113-122 and Lin, Chih-Hung, et al. "*Lasers as an approach for promoting drug delivery via skin.*" *Expert Opinion on Drug Delivery* 11.4 (2014): 599-614, the disclosures of which are herein incorporated by reference in their entirety.

Example drugs and substances reported in these references and suitable for use as a topical during RF treatment include: Nalbuphine and indomethacin; Morphine, nalbuphine and buprenorphine; 5-Aminolevulinic acid; Methotrexate; Lidocaine; Dextran; Oligonucleotides and plasmid DNA; Peptides and vaccine; Small interfering RNA and plasmid vector; $TiO_2$ nanoparticles (100 nm) and $Al_2O_3$ microparticles (27 μm); Vitamin C and magnesium ascorbyl phosphate; 3-O-ethyl ascorbic acid and ascorbic acid 2-glucoside; Diclofenac; Prednisone; ALA; Imiquimod, peptides and dextrans; Ovalbumin; ATG and basiliximab; CpG-adjuvanted allergen; Methyl ALA; Ascorbic acid 2-glucoside; Polyethylene glycol (400, 1000, 2050 and 3350 Da); siRNA and plasmid DNA; Dextran and quantum dots. Examples of drugs and substances reported to have enhanced skin penetration following physically enhancing treatments of the epidermis are provided in Benson, Heather AE, "*Transdermal drug delivery: penetration enhancement techniques.*" *Current drug delivery* 2.1 (2005): 23-33 and Cross et al., "*Physical enhancement of transdermal drug application: is delivery technology keeping up with pharmaceutical development?*" *Current drug delivery* 1.1 (2004): 81-92, the disclosures of which are herein incorporated by reference in their entirety.

One or more topicals may be applied prior to RF Fractional treatment to improve consistency of the electrical properties when RF fractional energy is applied to the treatment area. Topicals may also be applied such that they penetrate into the RF fractional injuries created by the RF fractional device treatment. In various embodiments, a single topical, such as moisturizer, may be used to improve one or more electrical or other properties during the delivery of RF energy. Topicals may be selected based on having enhanced tissue penetrating properties such as better penetration relative to tissue injuries created by the RF-based systems and methods disclosed herein. A given topical may be applied prior to treatment, reapplied during treatment, applied after treatment and combinations of the foregoing.

Of course, a multistep process may also be employed where there is a first course of topical application prior to treatment with the RF Fractional device and a second course of topical application to the RF fractional injuries having been created in the tissue. The topical applied in this multistep process can be the same topical or can be different topicals.

Finally, in some embodiments, the RF Fractional device is used to treat skin that has no topicals applied thereto and after RF fractional injuries are created in the tissue a topical may be applied to the RF fractional injuries.

Conditions addressed by using the RF Fractional device and topicals in concert include acne, melasma, acne scars, scars, wrinkles, uneven pigmentation, redness, and rosacea.

Figure 13:
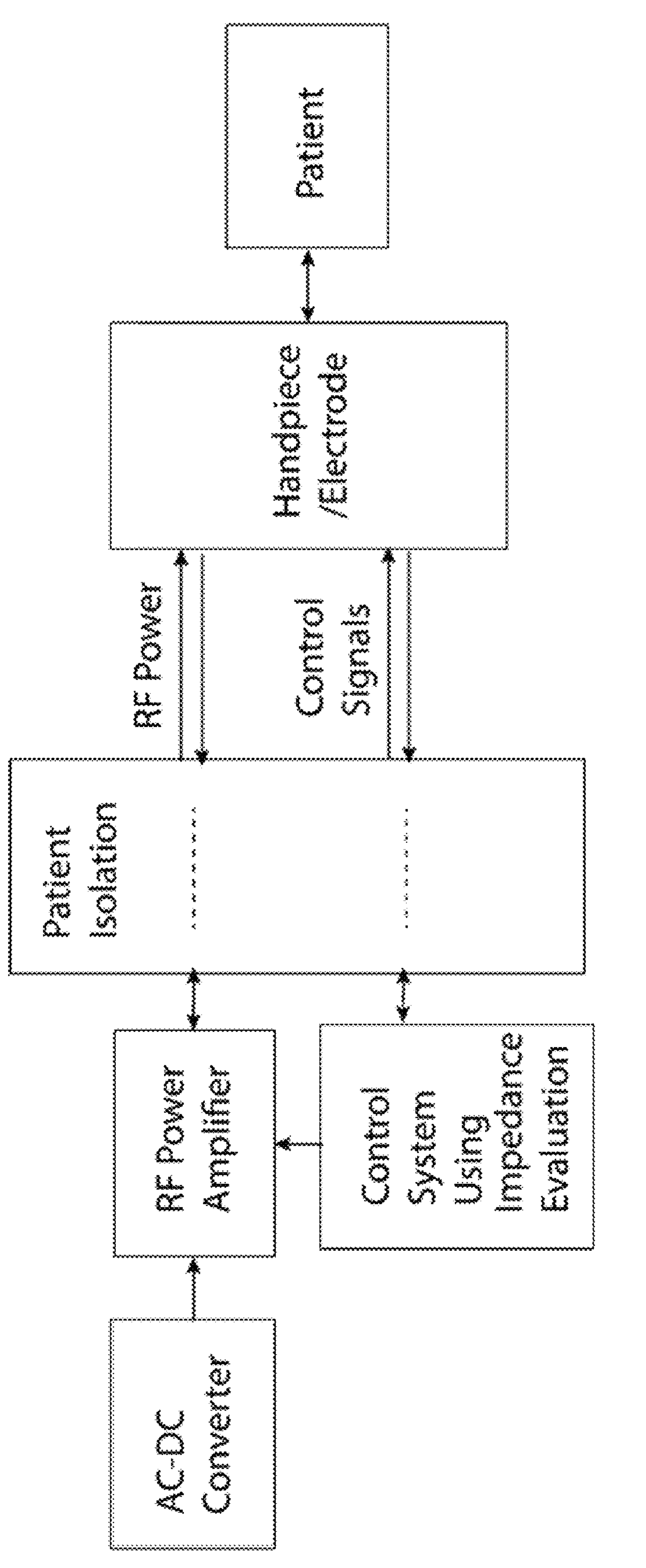
FIG. 13 is schematic diagram of an RF-based system suitable for controlling and delivering power and RF energy according to an illustrative embodiment of the disclosure.

FIG. 13 is a block diagram that shows a control system interacting with the impedance evaluation feedback around the impedance diagnostic during RF power delivery and treatment of a subject. In the system, AC power is converted to DC voltage in the AC to DC converter. The DC voltage is delivered to the RF power amplifier and then travels through the patient isolation component (e.g., a transformer). From patient isolation, the RF power is then delivered to the handpiece/electrode and the electrode array (see, e.g., FIGS. 1C, 2A, 4 and 5A-5C) that is attached to the handpiece (e.g., 1C and 2B-2D) and then RF power is delivered to the patient via the needles or non-penetrating needle electrodes (e.g., pins) of the array.

The RF power may be delivered in monopolar mode or bipolar mode or the single system may be capable of delivering both monopolar mode and bipolar mode (e.g., the Potenza™ RF microneedling system manufactured by Jeisys Medical, Inc. combines monopolar and bipolar RF at 1 or 2 MHz in a single device). The electrodes in the electrode array are also referred to as needles or blunt needles. The RF power can be delivered to the patient at a level suited for treating the condition of interest, e.g., skin rejuvenation or for creating fractional injuries that enhance topical penetration into the skin. Conditions addressed by topicals having enhanced penetration can include acne, melasma, acne scars, scars, wrinkles, uneven pigmentation, redness, and rosacea. The RF power range for treatment ranges from about 1 milliwatt to about 10 Kilowatts, or from about 100 milliwatts to about 500 Watts.

Optionally, not shown in FIG. 13, the DC voltage travels through the DC buck converter, which controllably converts the supplied DC voltage to the desired RF frequency. The controlled DC voltage is delivered to the RF power amplifier and then travels through patient isolation (e.g., a transformer). From patient isolation, the RF power is then delivered to the patient via the handpiece/electrode array as disclosed herein.

Therapeutic Treatment:

Referring still to FIG. 13, a single electrode or a select subset of single electrodes on the handpiece (in monopolar mode) or a subset of pairs of electrodes on the handpiece (in bipolar mode) are energized to therapeutically treat the area identified as benefitting from the desired treatment. In order to accomplish the therapeutic treatment, RF power is delivered to the patient via the electrodes present on the handpiece. The control system provides control signals that instruct that RF power be multiplexed through the arrays of electrodes present on the handpiece to the patient tissue.

In various embodiments, the control system multiplexes through single electrodes (in monopolar mode) or certain pairs of electrodes on the handpiece (in bipolar mode). For example, the RF power is delivered to the patient at a level suited for treating the condition of interest, e.g. skin rejuvenation or for creating fractional injuries that enhance topical penetration into the skin. Conditions addressed by topicals having enhanced penetration can include acne, melasma, acne scars, scars, wrinkles, uneven pigmentation, redness, and rosacea. The RF power range for treatment ranges from about 1 milliwatt to about 10 Kilowatts, or from about 100 milliwatts to about 500 Watts.

In general, the methods and systems disclosed herein may be used to provide various non-medical treatments such as cosmetic treatments, aesthetic treatments, and combinations thereof. Cosmetic treatment of tissue to rejuvenate skin or for creating fractional injuries that enhance topical penetration into the skin. These and other cosmetic treatments disclosed herein can improve the appearance and well-being of those that suffer with the foregoing conditions and others disclosed herein. In various embodiment, the disclosure relates to methods of controlling transmission of RF energy such that one or more tissue targets are cosmetically treated to reduce, prevent, reverse, or otherwise cosmetically treat one or more of the unwanted conditions disclosed herein.

Additional details relating to various systems for using RF and impedance sensing to treat tissue are disclosed in U.S. Publication No. 20200352633 entitled "NON-INVASIVE, UNIFORM AND NON-UNIFORM RF METHODS AND SYSTEMS RELATED APPLICATIONS", the entire disclosure of which is hereby incorporated by reference in its entirety.

Additional details relating to various systems for using RF and impedance sensing to treat tissue are disclosed in U.S. Publication No. 20190239939 entitled "METHODS AND APPARATUS FOR CONTROLLED RF TREATMENTS AND RF GENERATOR SYSTEM", the entire disclosure of which is hereby incorporated by reference in its entirety. Further, additional details relating to various systems for using RF and impedance sensing to treat tissue are disclosed in U.S. application Ser. No. 17/308,898 entitled "Needle-Array Devices and Related Methods", filed on May 5, 2021 the entire disclosure of which is hereby incorporated by reference in its entirety.

Systems and methods utilizing RF energy to treat an individual's skin (e.g., dermis and hypodermis) or other target tissue at a depth below a tissue surface with RF energy are described herein. In various aspects, the present teachings can provide a non-invasive, cooled (or uncooled) RF-based treatment to achieve one or more of body sculpting (lipolysis), sebaceous gland treatment, gland damage/deactivation, skin tightening (laxity improvement), cellulite treatment apparatus, vaginal laxity treatment or rejuvenation, urinary incontinence treatment, fecal incontinence treatment, and treatment of other genitourinary conditions, by way of non-limiting examples.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The following detailed description of embodiments is not to be regarded as limiting the scope of the applicant's teachings in any manner.

The terms "about" and "substantially" as used herein, refer to variations in a numerical quantity that can occur, for example, through measuring or handling procedures in the real world; through inadvertent error in these procedures; through differences/faults in the manufacture of electrical elements; through electrical losses; as well as variations that would be recognized by one skilled in the art as being equivalent so long as such variations do not encompass known values practiced by the prior art. Typically, the term "about" means greater or lesser than the value or range of values stated by 1/10 of the stated value, e.g., ±10%. For instance, applying a voltage of about +3V DC to an element can mean a voltage between +2.7V DC and +3.3V DC. Likewise, wherein values are said to be "substantially identical," the values may differ by up to 5%. Whether or not modified by the term "about" or "substantially" identical, quantitative values recited in the claims include equivalents to the recited values, e.g., variations in the numerical quantity of such values that can occur, but would be recognized to be equivalents by a person skilled in the art.

Moreover, nothing disclosed herein is intended to be dedicated to the public regardless of whether such disclosure is explicitly recited in the claims. To aid the Patent Office and any readers of any patent issued on this application in interpreting the claims appended hereto or otherwise presented throughout prosecution of this or any continuing patent application, applicants wish to note that they do not intend any claimed feature to be construed under or otherwise to invoke the provisions of 35 USC 112(f), unless the phrase "means for" or "step for" is explicitly used in the particular claim.

All of the drawings submitted herewith include one or more ornamental features and views, each of which include solid lines any of which also incorporate and correspond to and provide support for dotted lines and alternatively, each of which include dotted lines any of which also incorporate and correspond to and provide support for solid lines.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It should be appreciated that numerous changes can be made to the disclosed embodiments without departing from the scope of the present teachings. While the foregoing figures and examples refer to specific elements, this is intended to be by way of example and illustration only and not by way of limitation. It should be appreciated by the person skilled in the art that various changes can be made in form and details to the disclosed embodiments without departing from the scope of the teachings encompassed by the appended claims.

What is claimed is:

1. A method of cosmetic tissue treatment, comprising:

disposing a treatment applicator comprising an electrode array comprising a plurality of needles on a portion of tissue such that a region of the electrode array contacts the portion of tissue, wherein each needle is an electrode in electrical communication with a control system;

applying a pulse of radio frequency (RF) energy to the portion of tissue through the electrode array contacting the portion of tissue;

monitoring an impedance of the electrode array contacting the portion of tissue over time;

detecting a first impedance value of the electrode array before or during monitoring the impedances of the electrode array contacting the portion of tissue over time, wherein the first impedance value is detected before or during monitoring the impedances of the electrode array over time;

following the detection of the first impedance value, continuing monitoring changes to the impedance of the electrode array contacting the portion of tissue over time detecting an initial increase in impedance;

determining, while continuing monitoring impedance changes, that an impedance drop has occurred that meets or exceeds an expected threshold impedance drop while the electrode array is in contact with the portion of tissue following the initial increase in impedance;

initiating a treatment time period in response to the determining that the impedance drop has occurred that meets or exceeds the expected threshold impedance drop following the initial increase in impedance, wherein the monitored impedance changes of the electrode array over time correspond to impedance changes in the portion of the tissue in contact with the electrode array;

delivering treatment energy during the treatment time period using the plurality of needles, wherein delivery of the treatment energy is initiated by detecting that the impedance drop in the portion of tissue in contact with the electrode array has occurred that meets or exceeds the expected threshold impedance following the initial increase in impedance; and terminating application of the treatment energy after the treatment time period.

2. The method of claim 1, wherein a duration of the pulse is between about 1 ms and about 12 ms.

3. The method of claim 1, wherein the impedance of the electrode array over time is monitored at a sampling rate that ranges from about 10 KHz to about 50 KHz.

4. The method of claim 3 wherein the impedance of the electrode array over time is monitored at a sampling rate of about 30 KHz.

5. The method of claim 1 further comprising avoiding initiating muscle twitches during treatment time period.

6. The method of claim 5 wherein the electrode array has an output voltage with a ramp time ranging from about 100 microseconds to about 5 ms.

7. The method of claim 1 wherein the plurality of needles are connected in parallel.

8. The method of claim 1 further comprising transforming tissue such that tissue is removed in vicinity of contact with a subset of the plurality of needles.

9. The method of claim 1 further comprising applying a topical on the portion of the tissue prior to disposing the treatment applicator.

10. The method of claim 9 further comprising applying a topical on the portion of the tissue after the treatment time period.

11. The method of claim 9 wherein the topical is a skin moisturizer.

12. The method of claim 1 wherein the pulse of RF energy travels along surface of electrode and initiates a tissue effect when delivered to the portion of the tissue.

13. The method of claim 1 wherein one or more annular injuries is generated in tissue in response to the pulse of radio frequency (RF) energy.

14. The method of claim 1, wherein the impedance drop corresponds to a break down of one or more outer tissue layers of the portion of the tissue.

15. The method of claim 1, wherein the expected threshold impedance is selected to set a duration of the treatment time period or a portion thereof.

16. An apparatus for treating tissue, comprising:

a first treatment applicator head including a first plurality of needles;

an applicator body having a first end connected to the first treatment applicator head; and a control system;

wherein the applicator body includes a second end in communication with a radio frequency (RF) power source and the control system;

wherein the first treatment applicator head, when connected to the applicator body, is electrically connected with the RF power source in communication with the second end;

wherein the control system is configured to:

detect an initial increase in impedance determine, while monitoring impedance changes while the first plurality of needles contact a portion of the tissue, that an impedance drop has occurred that meets or exceeds an expected threshold impedance drop following the initial increase in impedance, and initiate a treatment time period in response to the determining that the impedance drop has occurred that meets or exceeds the expected threshold impedance drop following the initial increase in impedance, wherein the monitored impedance changes correspond to impedance changes in the portion of the tissue, wherein a timer for the treatment with RF energy is set by the control system in response to the impedance drop being detected following the initial increase in impedance, wherein the first plurality of needles is configured to deliver treatment energy during the treatment time period, wherein the control system terminates tissue treatment at end of the treatment time period.

17. The apparatus of claim 16 wherein each needle of the first plurality of needles has a blunt tip.

18. The apparatus of claim 16 further comprising a second treatment applicator head including a second plurality of needles, the first end of the applicator body connected to the second treatment applicator head, wherein the second treatment applicator head, when connected to the applicator body, is electrically connected with the RF power source.

19. A method of treating tissue comprising:

applying radio frequency (RF) power to tissue through a plurality of electrodes, the plurality of electrodes contacting a portion of the tissue, wherein each electrode is a needle in electrical communication with a control system;

during the application of the RF power, monitoring impedance changes of the plurality of electrodes over time;

detecting a first impedance value of the plurality of electrodes before or during monitoring impedances of the plurality of electrodes over time wherein the first impedance value is detected while monitoring the impedances of the electrode array over time;

following the detection of the first impedance value, continuing monitoring changes to the impedance of the electrode array contacting the portion of tissue over time detect an initial increase in impedance;

determining, while continuing monitoring impedance changes, that an impedance drop has occurred that meets or exceeds an expected threshold impedance drop while each needle is in contact with the portion of tissue, wherein the monitored impedance changes correspond to impedance changes in a portion of the tissue following the initial increase in impedance;

controlling the application of RF power based on the monitored impedance changes;

initiating a treatment time period in response to the determining that the impedance drop has occurred that meets or exceeds the expected threshold impedance drop following the initial increase in impedance, wherein the monitored impedance changes of the plurality of electrodes over time correspond to impedance changes in the portion of the tissue over time;

delivering treatment energy during the treatment time period using the plurality of electrodes, wherein delivery of the treatment energy is initiated by detecting that the impedance drop has occurred that meets or exceeds the expected threshold impedance following the initial increase in impedance; and terminating application of the treatment energy at the end of the treatment time period.

20. The method of claim 19, wherein the impedance drop that meets or exceeds the expected threshold impedance is correlated with one or more of the plurality of electrodes contacting an untreated region of tissue.

21. The method of claim 20 wherein a first conductive property of the untreated region of tissue differs from a second conductive property of a treated region of tissue.

22. The method of claim 21 wherein the treated region of tissue is disposed above the untreated region of tissue.

23. The method of claim 19, wherein RF power is reduced based on a reduction of impedance.

24. The method of claim 19, wherein the RF power is applied for a treatment time that ranges from about 1 ms to about 12 ms.

25. The method of claim 19, wherein the impedance drop ranges from about 10% to about 90% of the first impedance value.

26. The method of claim 19, wherein the impedance drop ranges from about 20% to about 50% of the first impedance value.

* * * * *